(12) United States Patent
Das et al.

(10) Patent No.: US 10,108,262 B2
(45) Date of Patent: *Oct. 23, 2018

(54) USER PHYSICAL ATTRIBUTE BASED DEVICE AND CONTENT MANAGEMENT SYSTEM

(71) Applicant: PAYPAL, INC., San Jose, CA (US)

(72) Inventors: Ananya Das, San Jose, CA (US); Shaun Warman, San Jose, CA (US); Bryant Luk, Round Rock, TX (US); Jason Ziaja, Cedar Park, TX (US); Christopher Diebold O'Toole, Cedar Park, TX (US)

(73) Assignee: PAYPAL, INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/790,859

(22) Filed: Oct. 23, 2017

(65) Prior Publication Data

US 2018/0107272 A1    Apr. 19, 2018

Related U.S. Application Data

(63) Continuation of application No. 15/169,195, filed on May 31, 2016, now Pat. No. 9,798,385.

(51) Int. Cl.
| | | |
|---|---|---|
| G09G 5/00 | (2006.01) |
| G06F 3/01 | (2006.01) |
| A61B 5/00 | (2006.01) |
| A61B 3/10 | (2006.01) |
| A61B 5/11 | (2006.01) |
| G02B 27/01 | (2006.01) |
| G06K 9/00 | (2006.01) |
| G06T 19/00 | (2011.01) |

(Continued)

(52) U.S. Cl.
CPC .............. *G06F 3/013* (2013.01); *A61B 3/101* (2013.01); *A61B 3/113* (2013.01); *A61B 3/14* (2013.01); *A61B 5/1103* (2013.01); *A61B 5/486* (2013.01); *A61B 5/4824* (2013.01); *G02B 27/0172* (2013.01); *G06K 9/00362* (2013.01); *G06T 19/006* (2013.01); *H04L 67/06* (2013.01); *G02B 2027/0138* (2013.01)

(58) Field of Classification Search
None
See application file for complete search history.

(56) References Cited

U.S. PATENT DOCUMENTS 5,570,698 A   11/1996   Liang et al.
7,435,226 B2   10/2008   Farbos (Continued)

*Primary Examiner* — Martin Mushambo
(74) *Attorney, Agent, or Firm* — Haynes and Boone, LLP

(57) ABSTRACT

Systems and methods for device and content management include determining a user is viewing virtual reality content from a user device, and receiving, through a network from the user device, body information associated with the user while the user is viewing the virtual reality content. A user device management configuration associated with the body information is determined. A user device management action is retrieved using the user device management configuration. A notification associated with the user device management action that causes the user device to perform the user device management action and modify the virtual reality content being viewed by the user is sent through the network to the user device.

20 Claims, 19 Drawing Sheets

(51) Int. Cl.
  *H04L 29/08*  (2006.01)
  *A61B 3/113*  (2006.01)
  *A61B 3/14*  (2006.01)

(56) References Cited

U.S. PATENT DOCUMENTS

| | | | |
|---|---|---|---|
| 7,435,227 B2* | 10/2008 | Farbos | A61B 3/113 |
| | | | 340/575 |
| 8,924,327 B2 | 12/2014 | Bazanov | |
| 8,957,835 B2 | 2/2015 | Hoellwarth | |
| 9,298,283 B1 | 3/2016 | Lin et al. | |
| 9,798,385 B1 | 10/2017 | Das et al. | |
| 9,843,768 B1 | 12/2017 | Negi et al. | |
| 2010/0128112 A1 | 5/2010 | Marti et al. | |
| 2010/0253689 A1 | 10/2010 | Dinicola et al. | |
| 2010/0295839 A1 | 11/2010 | Nagaya et al. | |
| 2011/0260967 A1* | 10/2011 | Matsushima | G02B 7/002 |
| | | | 345/156 |
| 2012/0052476 A1 | 3/2012 | Graesser et al. | |
| 2012/0197991 A1 | 8/2012 | Ramani et al. | |
| 2012/0204120 A1 | 8/2012 | Lefar et al. | |
| 2013/0154918 A1* | 6/2013 | Vaught | G06K 9/00617 |
| | | | 345/156 |
| 2013/0300759 A1 | 11/2013 | White | |
| 2014/0317561 A1 | 10/2014 | Robinson et al. | |
| 2014/0324749 A1 | 10/2014 | Peters et al. | |
| 2015/0121246 A1 | 4/2015 | Poore et al. | |
| 2015/0363979 A1 | 12/2015 | Takano et al. | |
| 2016/0004299 A1 | 1/2016 | Meyer et al. | |
| 2016/0324416 A1 | 11/2016 | Fateh | |
| 2016/0334868 A1 | 11/2016 | Pacheco et al. | |
| 2016/0350609 A1 | 12/2016 | Mason et al. | |
| 2016/0350977 A1 | 12/2016 | Doronichev et al. | |
| 2017/0156586 A1 | 6/2017 | Fateh | |
| 2017/0237848 A1 | 8/2017 | Davis et al. | |
| 2017/0287215 A1 | 10/2017 | Lalonde et al. | |
| 2017/0344109 A1 | 11/2017 | Das et al. | |

* cited by examiner

MANAGEMENT CONFIGURATIONS

USER DEVICE MANAGEMENT CONFIGURATIONS 306

| PRE-EXISTING HEALTH CONDITIONS 308 | | VIRTUAL REALITY DEVICE 310 | | DESKTOP DEVICE 312 | | HAND-HELD DEVICE 314 | |
|---|---|---|---|---|---|---|---|
| | | SESSION LENGTH | BREAK LENGTH | SESSION LENGTH | BREAK LENGTH | SESSION LENGTH | BREAK LENGTH |
| NONE | | 35 min | 10 min | 20 min | 5 min | 40 min | 5 min |
| LASIK | | 30 min | 10 min | 40 min | 10 min | 40 min | 10 min |
| NEARSIGHTED | >= -4.00 | 20 min | 10 min | 50 min | 5 min | 40 min | 10 min |
| | < -4.00 | 30 min | 8 min | 40 min | 5 min | 30 min | 10 min |
| FARSIGHTED | <= +4.00 | 30 min | 10 min | 50 min | 5 min | 40 min | 5 min |
| | > +4.00 | 20 min | 7 min | 40 min | 5 min | 30 min | 5 min |

USER DEVICE 300

FIGURE 3

MANAGEMENT CONFIGURATIONS

USER DEVICE MANAGEMENT CONFIGURATIONS 402

| BODY INFORMATION 404 | PRE-EXISTING HEALTH CONDITIONS 308 | USER DEVICE MANAGEMENT ACTIONS 406 |
|---|---|---|
| BLINKING /SQUINTING RATE > 20 TIMES/MIN | NONE | DISPLAY A BREAK REMINDER; PROVIDE A NOTIFICATION ABOUT ADJUSTING SCREEN BRIGHTNESS |
| | LASIK | AUTOMATICALLY SWITCH TO SLEEP MODE FOR 10 MINUTES |
| EYE DRYNESS > DRYNESS THRESHOLD | NEARSIGHTED >= -4.00 | PROVIDE A NOTIFICATION INDICATING A HIGH LEVEL OF EYE DRYNESS |
| | < -4.00 | |
| HEADACHE GESTURES | | DISPLAY A BREAK REMINDER |
| | | AUTOMATICALLY SWITCH TO SLEEP MODE FOR 5 MINUTES |
| HEART RATE > HEARTRATE THRESHOLD | HEART DISEASE | AUTOMATICALLY SWITCH TO SLEEP MODE FOR 10 MINUTES |

USER DEVICE 300

FIGURE 4

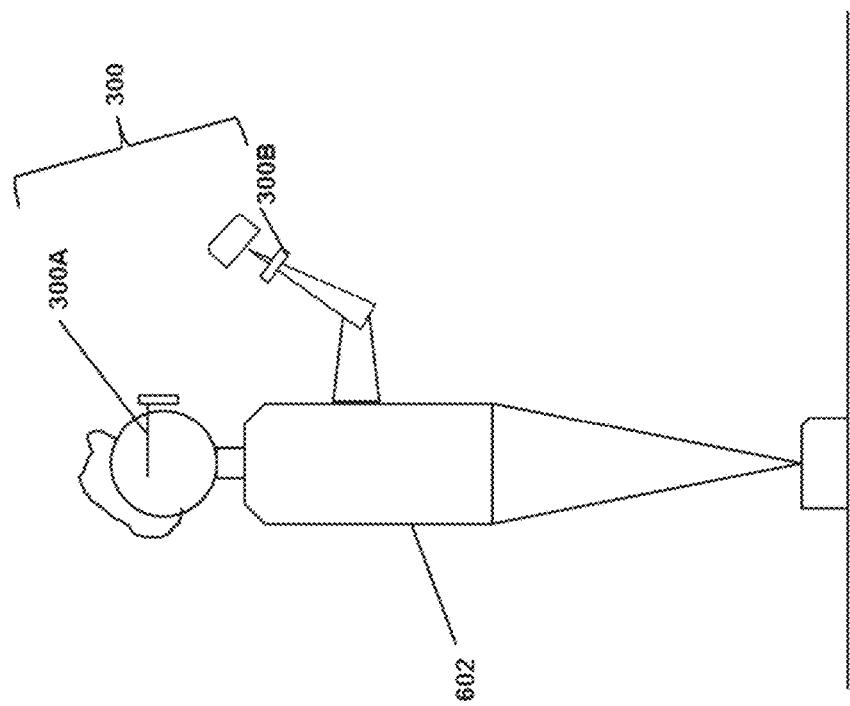

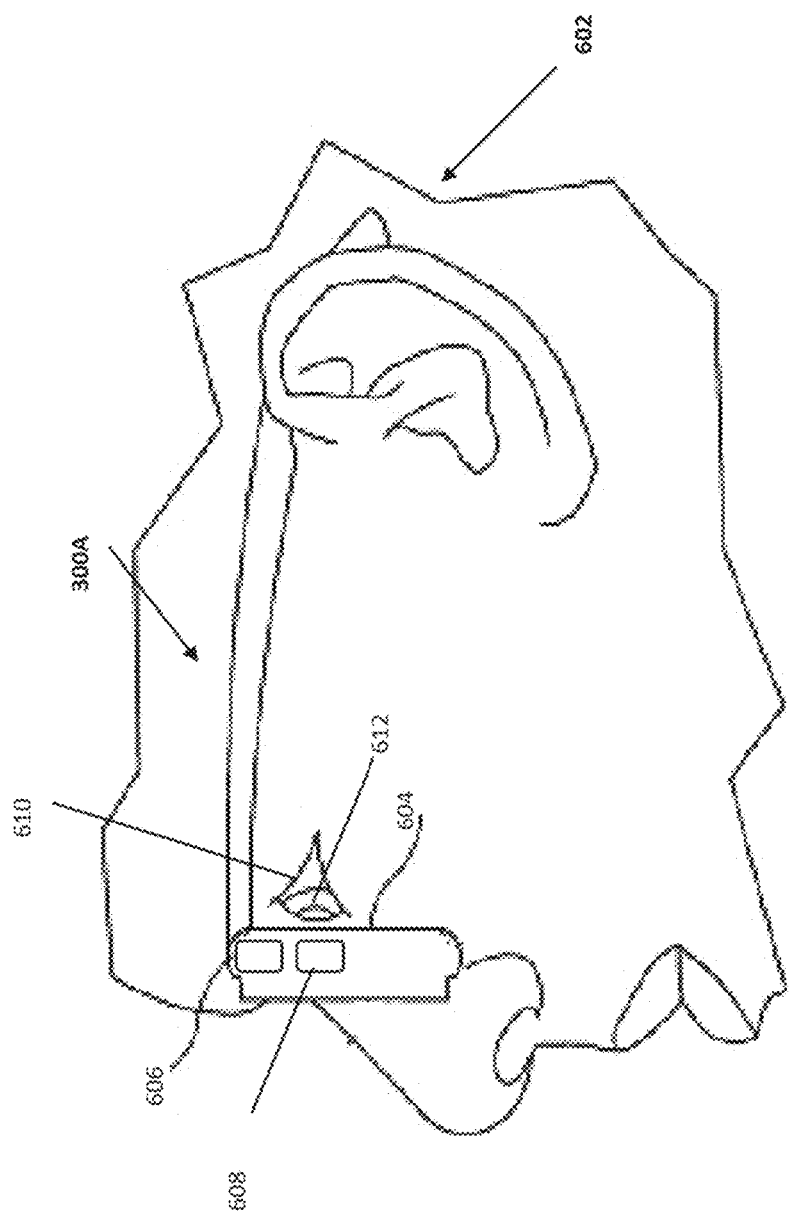

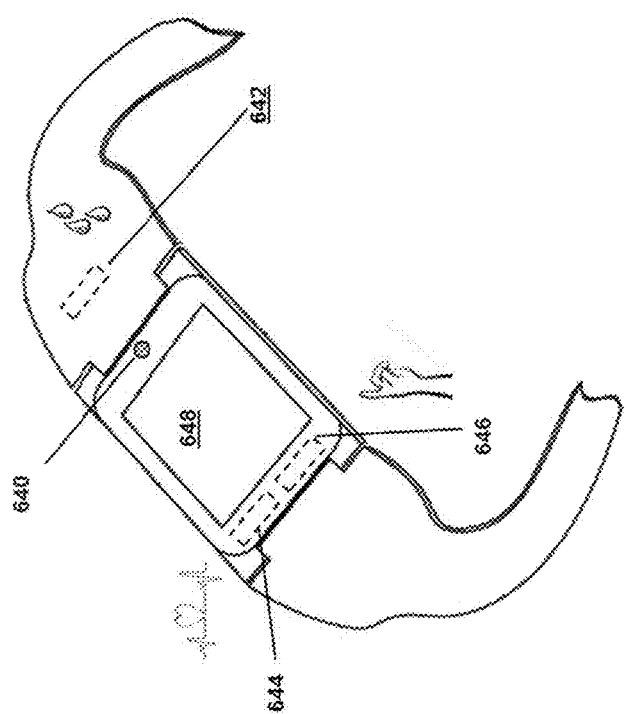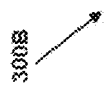

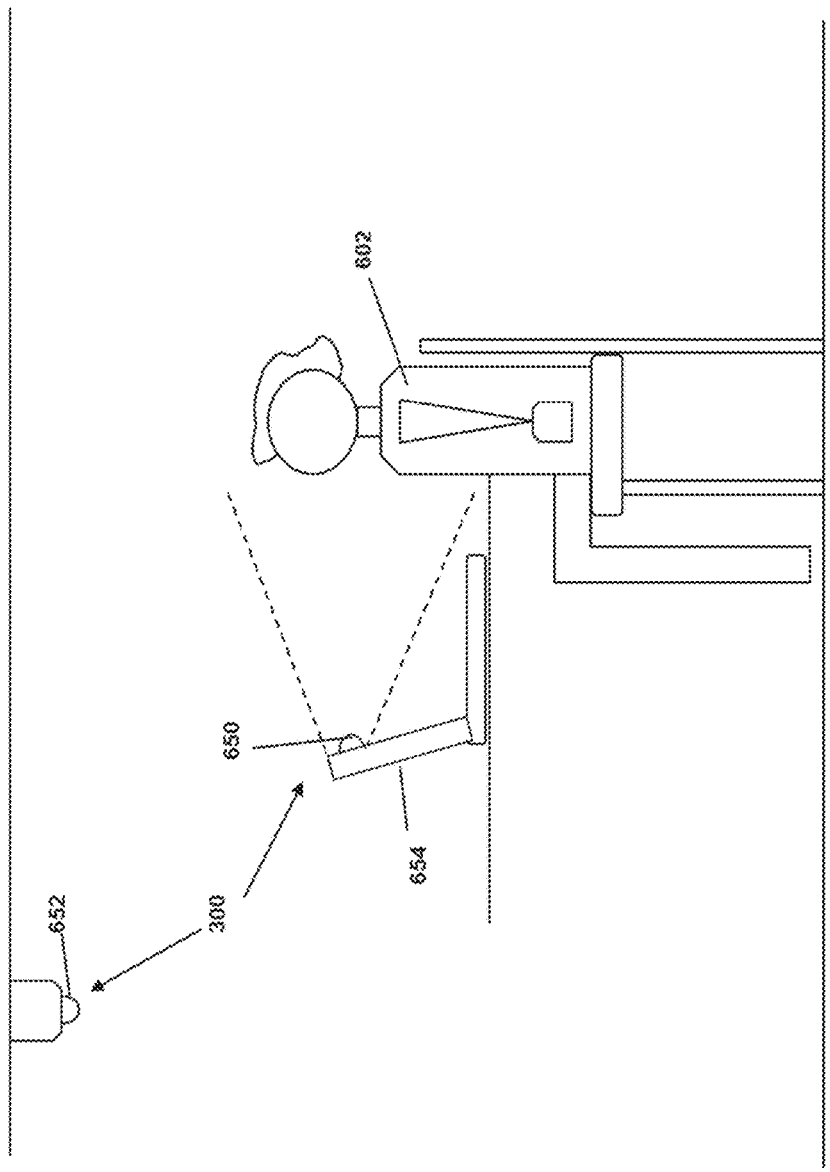

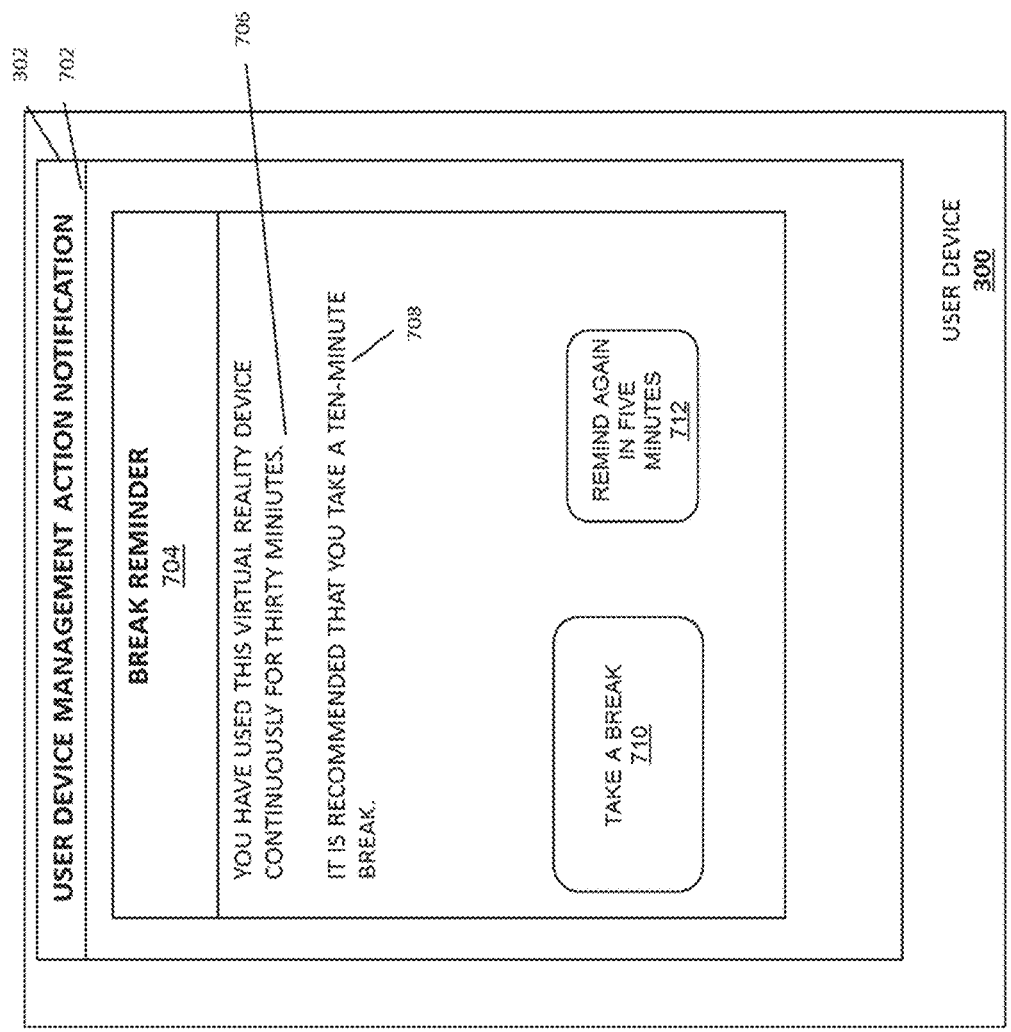

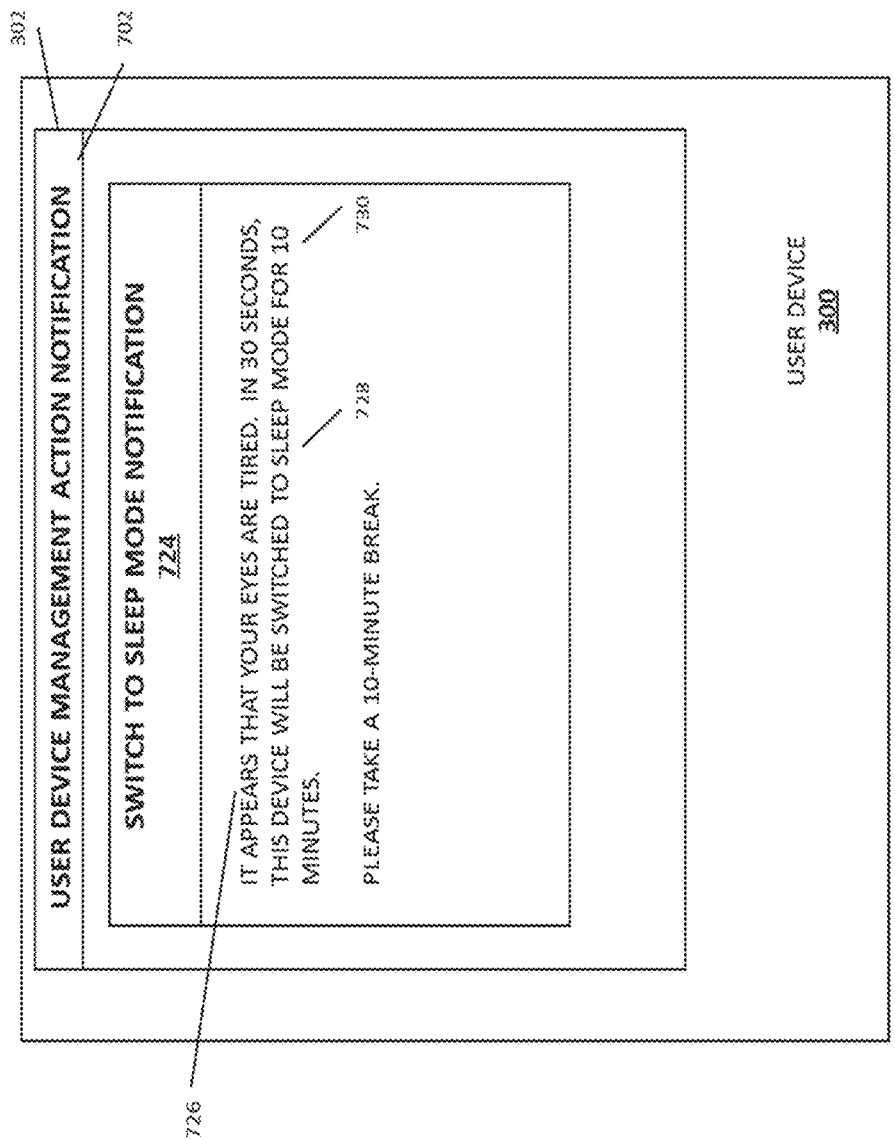

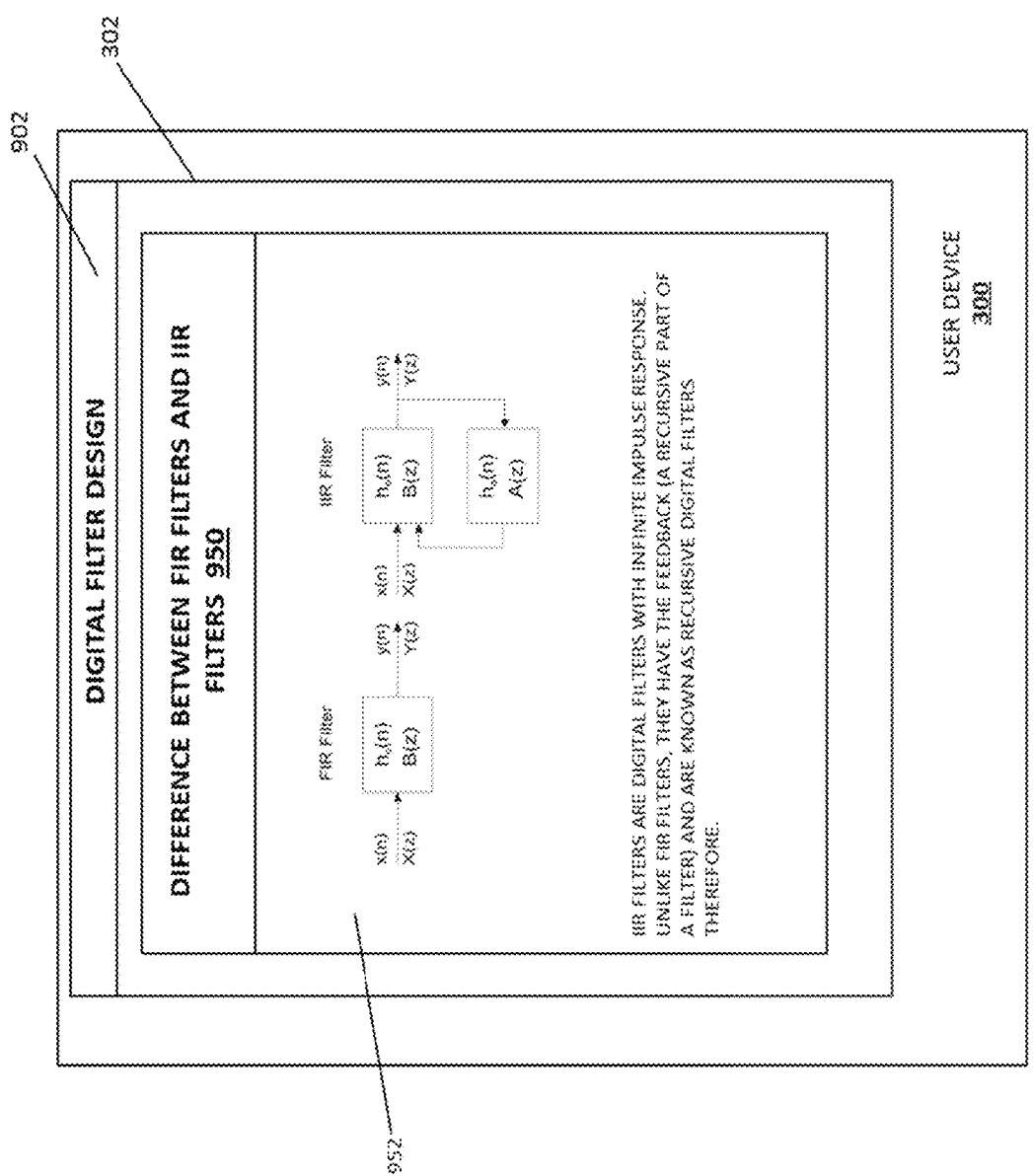

USER PHYSICAL ATTRIBUTE BASED DEVICE AND CONTENT MANAGEMENT SYSTEM

CROSS-REFERENCE TO RELATED APPLICATIONS

This is a Continuation Application to U.S. Utility application Ser. No. 15/169,195 filed May 31, 2016, entitled "USER PHYSICAL ATTRIBUTE BASED DEVICE AND CONTENT MANAGEMENT SYSTEM," the disclosure of which is incorporated herein by reference in its entirety.

BACKGROUND

The present disclosure generally relates to device and content management, and more particularly to a device and content management system that manages devices and content displayed on those devices using user physical attribute information of users of the devices.

The Internet has allowed users with computing devices to exchange and utilize a variety of information. For example, users may receive various content such as course materials or other educational material using the Internet, and take educational courses taught online via the Internet. However, such online courses may be impersonal and un-stimulating to many users. For example, it may be challenging for teachers of such online courses to judge the students' understanding of the course materials in real time. Furthermore, students of online courses are often not proactive, and as such often do not seek out help or ask questions about course materials they may not understand. The lack of student engagement in such online courses compared to in-person classrooms may negatively affect the online courses' effectiveness, and may result in student users abandoning those online courses. Moreover, while various technologies in devices (e.g., head-mounted devices such as virtual reality devices, hand-held devices, etc.) may be used to enhance a student user's experience, prolonged use of such devices may cause discomfort (e.g., eye strain, headaches, neck pain, etc.) to the users, and can raise health concerns for the users as well.

Thus, there is a need for a device and content management system that addresses the issues detailed above.

BRIEF DESCRIPTION OF THE FIGURES

FIG. 3 is a screen shot illustrating an embodiment of a user device displaying a user device management configurations screen;

FIG. 4 is a screen shot illustrating an embodiment of a user device displaying a user device management configurations screen;

FIG. 6A is a schematic illustrating an embodiment of a user using one or more user devices;

FIG. 6B is a schematic illustrating an embodiment of a user device;

FIG. 6C is a schematic illustrating an embodiment of a user device;

FIG. 6D is a schematic illustrating an embodiment of a user using one or more user devices;

FIG. 7A is a screen shot illustrating an embodiment of a user device displaying a break reminder screen;

FIG. 7B is a schematic view illustrating an embodiment of a user device displaying a switch to sleep mode notification screen;

FIG. 9B is a screen shot illustrating an embodiment of a user device displaying an online course screen;

Figure 1:
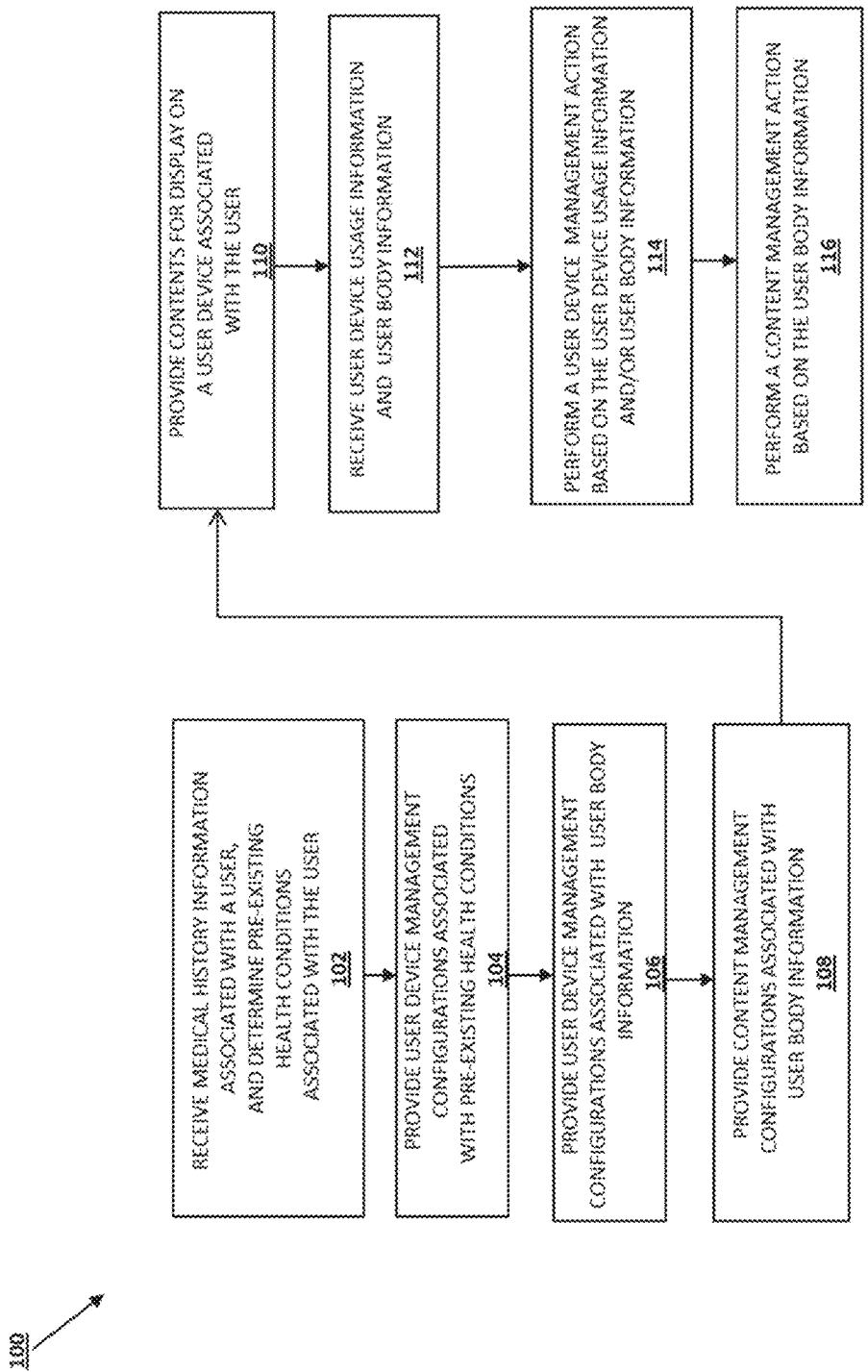
FIG. 1 is a flow chart illustrating an embodiment of a method for device and content management.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

The present disclosure describes a system and method for providing device management and content management to one or more user devices. Various user devices may be used by the user to perform various tasks such as, for example, taking an online course, playing computer games, reading news/blogs, shopping, and/or engaging in online transactions. Those user devices may be configured to capture physical attributes or other body information of the user while the user is performing these tasks. In various embodiments, the physical attributes or other body information may include facial information (e.g., eye redness, eye dryness, eye size, blinking rate, yawn) of the user, gesture information (e.g., raising a hand, nodding off), and/or body measurement data associated with measurements of the user's physical attributes or body functions (e.g., heart rate, temperature, perspiration rate). The body information detected from the user devices may provide health information (e.g., eye strain, headache, neck pain) of the user. Such health information, together with medical history information (e.g., eye prescriptions) of the user, may be used to determine a variety of recommendations to be made to the user such as, for example, that the user needs to take a break from using the user device. In addition to recommendations, a user device management action for controlling the user device (e.g., switching to sleep mode, reducing brightness with one or more images and/or texts, increasing brightness with one or more images and/or texts, increasing or decreasing text and/or image sizes, reducing or increasing speed of content or image changes or transitions) may also be performed. Furthermore, the body information from the user devices may be analyzed to provide user engagement information (e.g., degree of attention and/or interest, request for seeking help/asking questions, etc.) associated with content (e.g., online courses, computer games, news/blogs, shopping items, online transactions, etc.) displayed on the user devices, which may be used to manage the content displayed and/or otherwise provided to the user via the user device.

Figure 2:
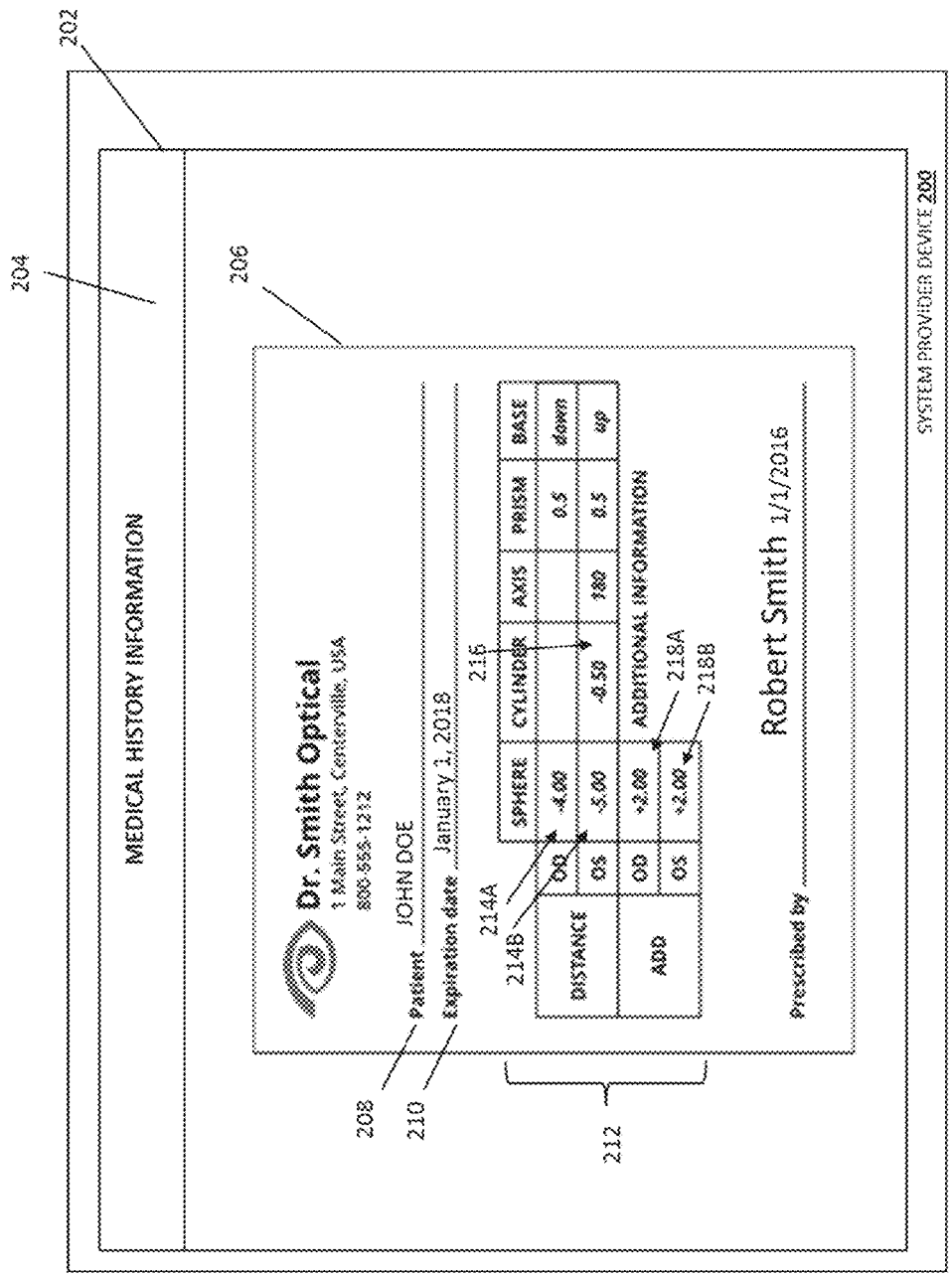
FIG. 2 is a screen shot illustrating an embodiment of a system provider device displaying a medical history information screen.

Referring to FIG. 1, an embodiment of a method 100 for providing device and content management is illustrated. Referring to FIGS. 1 and 2, the method 100 may begin at block 102 where a system provider device receives medical history information associated with a user, and determines pre-existing health condition information associated with the user based on the medical history information. Referring to FIG. 2, an embodiment of a system provider device displaying a medical history information screen is illustrated. As illustrated in FIG. 2, the system provider device 200 includes a display 202 displaying a medical history information screen 204. The medical history information screen 204 displays medical history information about the user received by the system provider device 200 (e.g., from a medical history service provider, from a medical history database coupled to the system provider device 200, and/or from the user or a person (e.g., a parent) associated with the user). In the example of FIG. 2, the medical history information includes a lens prescription 206. The lens prescription 206 may be a contact lens prescription or an eyeglasses prescription.

In the example illustrated in FIG. 2, the lens prescription 206 is an eyeglasses prescription, and is referred to as the eyeglasses prescription 206 below. The eyeglasses prescription 206 provides a user identifier 208 (e.g., the patient "JOHN DOE"), and an expiration date 210 (e.g., "Jan. 1, 2018") of the eyeglasses prescription. At block 102, the system provider device 200 analyzes the eyeglasses prescription 206 to generate pre-existing health condition information 212 associated with the user. In some examples, the pre-existing health condition information 212 includes nearsightedness information 214A and 214B. The nearsightedness information 214A in FIG. 2 indicates that the right eye ("OD") of the user has a nearsightedness that may be corrected by a lens having a −4.00 diopter spherical power, while the nearsightedness information 214B indicates that the left eye ("OS") of the user has a nearsightedness that may be corrected by a lens having a −5.00 diopter spherical power. In some examples, the pre-existing health condition information 212 may include nearsighted astigmatism information 216 indicating that the left eye of the user has nearsighted astigmatism that may be corrected by a lens having a −0.50 cylindrical power. In some examples, the pre-existing health condition information 212 includes near-addition information 218A and 218B. The near-addition information 218A may indicate additional correction information (e.g., "+2.00") required for reading for the right eye, and the near-addition information 218B may indicate additional correction information (e.g., ("+2.00") required for reading for the left eye.

It is noted that while an eyeglasses prescription is used as an example of medical history information, it is not intended to be limiting. The medical history information may include various medical records associated with a variety of pre-existing eye health conditions (e.g., laser-assisted in situ keratomileusis (LASIK) operation records, contact lens prescriptions, and/or other eye-health conditions known in the art) and/or other pre-existing health conditions (e.g., pre-existing balance and coordination conditions, pre-existing ear/hearing health conditions, pre-existing heart disease conditions, heart disease drug prescriptions, and/or other health conditions known in the art), which may be received and analyzed by the system provider device 200 to generate various health condition information associated with the user.

Referring to FIGS. 1 and 3, the method 100 may proceed to block 104 where user device management configurations associated with health condition information are provided. In some embodiments, the user device management configurations may be default configurations provided by the system provider device 200 and may be applicable to a plurality of users. In some embodiments, the user device management configurations may be configured by a user or a person associated with the user (e.g., a parent of the user), and thus may be customized for a single user or a group of users (e.g., users having an age between ten and twelve years old).

In some embodiments, the user device management configurations may include configurations for managing different components of the user device. In some examples, the user device management configurations may be associated with controlling various graphics and/or display properties (e.g., brightness, contrast, color depth, and/or other display properties know in the art) of the user device based on health conditions (e.g., pre-existing eye health conditions or other health conditions) of the user. In some examples, the user device management configurations may be associated with controlling sound properties (e.g., headphone volume, speaker volume, and/or audio properties such as bass, treble, etc.) of the user device based on the health conditions (e.g., health conditions associated with the user's ears) of the user. In some embodiments, the user device management configurations may include configurations that may be used to control a duration of a continuous usage session (also know as a "session length") that the user may use the user device, and/or a duration of a break (also known as a "break length") between two continuous usage sessions that the user may take based on various health conditions of the user (e.g., by dimming a display of the user device, putting the user device in a sleep mode, shutting the user device down, and/or other actions that would be apparent to one of skill in the art in possession of the present disclosure).

Referring to FIG. 3, illustrated is an embodiment of a user device displaying a user device management configurations screen that includes user device management configurations. The user device 300 includes a display 302 displaying a user device management configurations screen 304 provided by the system provider device that includes a user device management configurations section 306. The user device management configurations section 306 includes user device management configurations 316, 318, 320A, 320B, 322A, and 322B associated with different pre-existing health conditions 308 respectively.

In some embodiments, the user device management configuration may include different configurations associated with different types of user devices (e.g., head-mounted devices such as virtual reality devices, desktop devices, laptop devices, hand-held devices (e.g., phones, tablets), and any other types of user devices known in the art). Various user devices of different types may have different viewing distance (e.g., distances between displays of the devices and the users' eyes) and image characteristics (e.g., font sizes), and the use of those user devices may affect the user differently. For example, a viewing distance for a head-mounted device is about 15 to 30 millimeters, a viewing distance for a desktop device is between about 400 to 700 millimeters, and a viewing distance for a hand-held device is between about 170 to 500 millimeters. As such, a user may experience eye strain more quickly using a head-mounted device relative to using a desktop device. Accordingly, different user device management configurations for different types of user devices may be provided. In some examples, for a user that has no health conditions of concern, the user device management configuration 316 may include a head-mounted device management configuration 310 that provides that, if the user device is a head-mounted device, the user needs to take at least a ten-minute break after a continuous usage session of about 35 minutes; a desktop device management configuration 312 that provides that if the user device is a desktop device, the user needs to take at least a five-minute break after a continuous usage session of about 50 minutes; and a hand-held device management configuration 314 that provides that if the user device is a hand-held device, the user needs to take at least a five-minute break after a continuous usage session of about 40 minutes. The time limit may also be based on the type of content being displayed, including how fast images are changing, how bright or intense the images are, and any other factors that may affect eye health. In some examples, for a user with a health condition 308 that includes having received LASIK eye surgery, a user device management configuration 318 provides that the user needs to take breaks more often and/or take longer breaks compared to other users who have not received LASIK eye surgery. For example, a desktop device management configuration 312 of the user device management configuration 318 provides that if the user has received LASIK eye surgery, the user needs to take at least a ten-minute break for every forty minutes using a desktop user device.

In some embodiments, for a user with a pre-existing health condition 308 of nearsightedness or farsightedness, the corresponding user device management configurations 320A, 320B, 322A, and 322B may include different configurations associated with different degrees of nearsightedness or farsightedness. For example, a user device management configuration 320A is associated with a low degree nearsightedness (e.g., with an eyeglasses prescription of ≥−4.00 diopter spherical lens power), and provides user device management configurations for a user having such a relatively low degree nearsightedness. For further example, a user device management configuration 320B is associated with a higher degree farsightedness (e.g., with an eyeglasses prescription of less than −4.00 diopter spherical lens power), and provides user device management configurations for a user having such a relatively higher degree nearsightedness. Similarly, user device management configurations 322A and 322B are associated with a relatively low degree of farsightedness (e.g., with an eyeglasses prescription of ≤=+4.00 diopter spherical lens power) and a relatively higher degree of farsightedness (e.g., with an eyeglasses prescription of greater than +4.00 diopter spherical lens power), respectively.

Referring to FIGS. 1 and 4, the method 100 may proceed to block 106 where user device management configurations associated with user body information are provided. For example, the user body information may be associated with the user's current health condition such as pain or discomfort resulted from prolonged use of the user device. The user device management configurations may be used to provide various user device management actions to control the user device usage based on the user's current health condition, pre-existing health condition, and/or combinations thereof. Referring to FIG. 4, illustrated is an embodiment of a user device displaying a user device management configurations screen identifying user device management configurations associated with body information. The user device 300 includes a display 302 displaying a user device management configurations screen 304 provided by the system provider device that includes a user device management configurations section 402. The user device management configurations section 402 includes user device management configurations 408, 410, 412, 414, 416, and 418 associated with different user body information 404 (also referred to as body information 404) and health conditions 308.

In some embodiments, the body information includes facial information associated with the user's current health conditions. For example, user device management configurations 408 and 410 are associated with user body information 404 that includes facial information (e.g., "BLINKING/SQUINTING RATE>20 TIMES/MIN"). Such facial information includes a relatively high blinking and/or squinting rate (e.g., greater than 20 times/minute), which may be associated with a current health condition indicating that the user is experiencing eye discomfort. The user device management configuration 408 provides that in response to receiving such body information for a user associated with no pre-existing health conditions of concern, the system provider device 200 may cause the user device to perform a user device action 406 and display a break reminder. The user device management configuration 410 also provides that in response to receiving such body information for a user associated with a pre-existing health condition 308 indicating that the user received LASIK eye procedure, the system provider device may cause the user device to perform a user device action 406 where the user device automatically switches to a sleep mode and sleeps for ten minutes.

In the example of FIG. 4, user device management configuration 412 is associated with user body information 404 that includes facial information (e.g., "EYE DRYNESS>DRYNESS THRESHOLD"). The facial information is associated with a current user health condition indicating that the user has a relatively high-level of eye dryness (e.g., having a dryness level higher than a dryness threshold). In some examples, the dryness threshold may be determined during a training period when the user does not experience any eye discomfort. In some examples, the dryness threshold may be determined based on eye health conditions of the user (e.g., a dryness threshold for a user received LASIK eye procedure may be lower than another user who has not received LASIK eye procedure). The user device management configuration 412 provides that regardless of the user's pre-existing health conditions, for a user with a relatively high-level of eye dryness, the system provider device 200 may cause the user device to perform a user device action 406 to display a notification indicating that the user is experiencing a relatively high level of eye dryness.

In some embodiments, the body information includes gesture information associated with gestures of the user. For example, user device management configurations 414 and 416 are associated with user body information 404 that includes gesture information (e.g., "HEADACHE GESTURES"). The gesture information is associated with gestures (e.g., using a hand to massage the forehead) associated with the user's current health condition, which indicates that the user may be experiencing a headache. In some embodiments, user device management configurations 414 and 416 include different user device actions 406 for different pre-existing health conditions 308 associated with the user. For example, user device management configuration 414 provides that for a user associated with a health condition 308 that includes a relatively low degree of nearsightedness (e.g., with an eyeglasses prescription of greater than or equal to −4.00 diopter spherical lens power), the system provider device may cause the user device to perform a user device action 406 and display a break reminder. For further example, user device management configuration 416 provides that for a user associated with a health condition 308 that includes a relatively high degree of nearsightedness (e.g., with an eyeglasses prescription of less than −4.00 diopter spherical lens power), the system provider device may cause the user device to perform a user device action 406 where the user device automatically switches to a sleep mode for five minutes.

In some embodiments, the body information includes body measurement data associated with the user. For example, user device management configuration 418 is associated with user body information 404 that includes body measurement data (e.g., "HEART RATE>HEARTRATE THRESHOLD") associated with the user's current health condition (e.g., the user is getting too excited and may be subject to an increased heart attack risk) given the user's pre-existing health conditions 308 (e.g., "HEART DISEASE"). The user device management configuration 418 provides that in response to receiving such body measurement data, the system provider device may cause the user device to perform a user device action 406 where the user device automatically switches to a sleep mode for about 10 minutes.

In various embodiments, the user device action may be determined based on the type of content being displayed, including how fast images are changing, how bright or intense the images are, image and/or text sizes, and any other factors that may affect eye health. In an example, such user device action may include reducing brightness with one or more images of the content. In another example, such user device action may include increasing brightness with one or more images of the content. In yet another example, such user device action includes increasing or decreasing text and/or image sizes. In yet another example, such user device action includes reducing or increasing speed of content or image changes or transitions.

Figure 5:
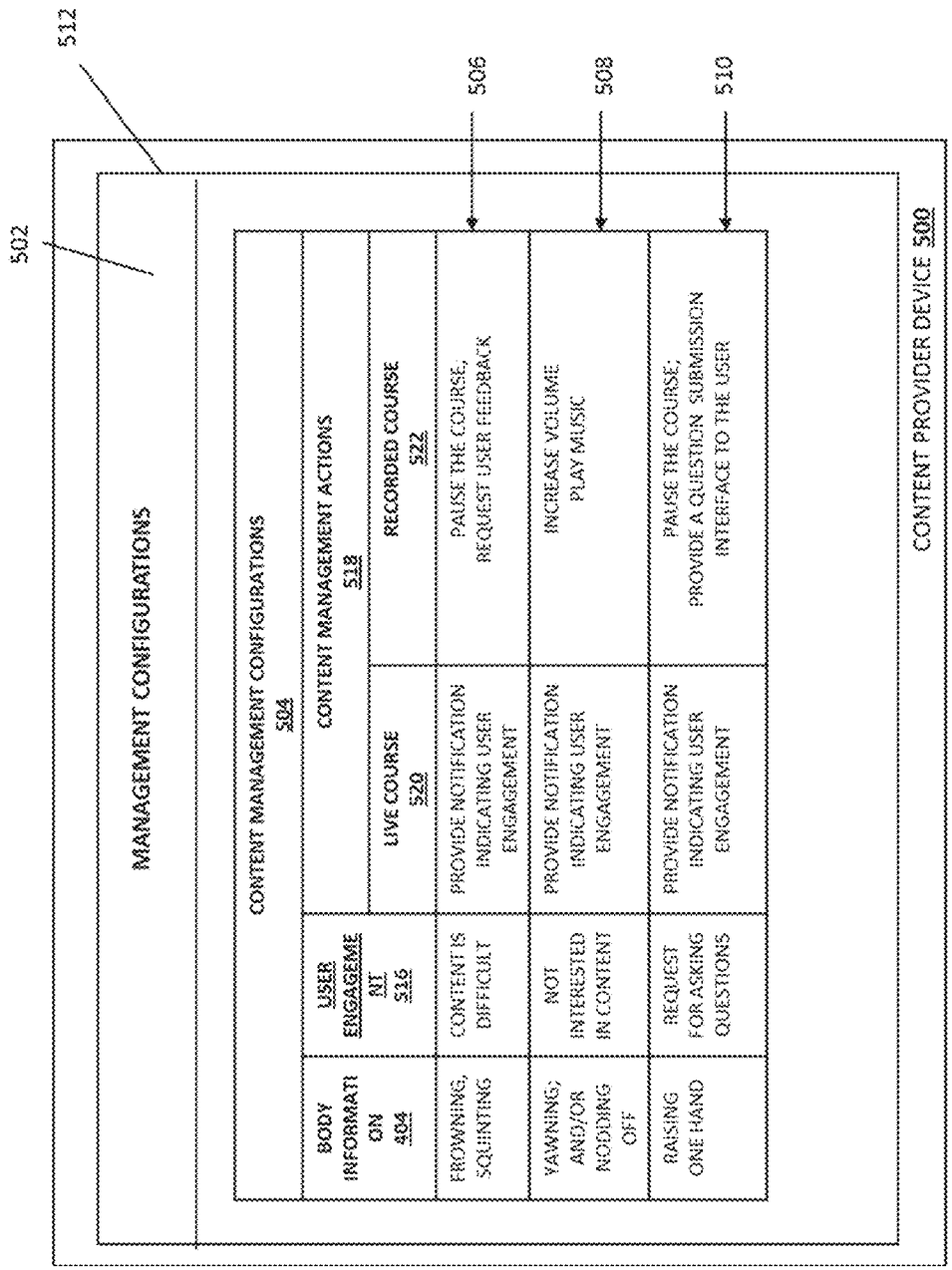
FIG. 5 is a screen shot illustrating an embodiment of a content provider device displaying a content management configurations screen.

Referring to FIGS. 1 and 5, the method 100 may proceed to block 108 where content management configurations associated with body information are provided. Such body information may be associated with user engagement information (e.g., a content difficulty level, a user interest level, and/or other user engagement information that would be apparent to one of skill in the art in possession of the present disclosure) associated with the content displayed on the user device. A system provider device may then perform content management actions to manage the content displayed on the user device based on the user engagement information in order to improve user engagement with that content.

Referring to FIG. 5, illustrated is an embodiment of a content provider device displaying a content management configurations screen including content management configurations associated with body information. The content provider device 500 includes a display 512 displaying a content management configurations screen 502 provided by the system provider device that includes a content management configurations section 504. The content management configurations section 504 includes content management configurations 506, 508, and 510 associated with different user body information 404.

In some embodiments, a content management configuration is associated with body information including facial information, gesture information, and/or combinations thereof. In an example, content management configuration 506 is associated with user body information 404 including facial information (e.g., "FROWNING, SQUINTING"), which is associated with user engagement information 516 (e.g., "CONTENT IS DIFFICULT") and may indicate that the user may find that the content currently being displayed is presenting some difficulties to the user. In another example, content management configuration 508 is associated with body information 404 including facial information (e.g., "YAWNING") and/or gesture information (e.g., "NODDING OFF"), which is associated with user engagement information 516 (e.g., "NOT INTERESTED IN CONTENT") indicating that the user is not interested in the content currently being displayed. In yet another example, content management configuration 510 is associated with body information 404 including gesture information (e.g., "RAISING ONE HAND"), which is associated with user engagement information 516 (e.g., "REQUEST FOR ASKING QUESTIONS") indicating that the user may have questions to ask about the content currently being displayed.

In some embodiments, a content management configuration includes different configurations associated with different types of content (e.g., content provided in live courses, content provided in recorded courses, news content, blog content, computer gaming content, shopping item content, online instruction manual content, and/or other content known in the art) provided by various content providers, and provide different content management actions accordingly. In some examples, as illustrated in FIG. 5, each of the content management configurations 506, 508, and 510 includes a live course management action 520 associated with live course content provided by the content provider device 500 (e.g., live course content provided with a teacher to users in real-time in a physical classroom and/or an online classroom), and a recorded course management action 522 associated with a course using recorded material content provided by the content provider device 500.

In some embodiments, a content management configuration is associated with body information including both facial information and gesture information. For example, content management configuration 508 is associated with body information 514 that includes facial information (e.g., "YAWNING") and gesture information (e.g., "NODDING OFF") that may indicate that the user may have lost interest in the content currently being displayed. In such examples, a live course management action 520 of the content management configuration 508 provides that if the content is associated with live course content and the particular body information (e.g., "YAWNING" and/or "NODDING OFF") associated with the user is detected, a notification indicating that the user is losing interest in the content is provided to the teacher provided for the live course content (e.g., on a teacher device). A recorded course management action 522 of the content management configuration 508 provides that if the content is associated with recorded course content, when the particular body information (e.g., "YAWNING" and/or "NODDING OFF") associated with the user is detected, the content provider device 500 may automatically adapt the content displayed on a display of the user device based on the particular body information. For example, the content provider device 500 may increase the volume of the content displayed on the user device, play music on the user device, and/or perform other actions to stimulate interest or attention to the content.

In some embodiments, a content management configuration is associated with body information including gesture information. For example, content management configuration 510 is associated with body information 514, which includes gesture information (e.g., "RAISING ONE HAND") that may indicate that the user is requesting to ask a question. In such examples, a live course management action 520 of the content management configuration 508 provides that if the content is associated with live course content and the particular body information (e.g., "RAISING ONE HAND") associated with the user is detected, a notification indicating that the user is requesting to ask a question is provided to the teacher provided for live course content (e.g., on a teacher device). A recorded course management action 522 of the content management configuration 508 provides that if the content is associated with recorded course content and the particular body information (e.g., "RAISING ONE HAND") associated with the user is detected, the content provider device 500 may automatically pause the content displayed on a display of the user device, and provide a submit question screen allowing the user to submit one or more questions about the content currently being displayed.

Referring to FIGS. 1, 6A, 6B, 6C, and 6D, the method 100 proceeds to block 110, where content is provided for display on a user device associated with the user. In various embodiments, the user device may receive the content from the system provider device, a content provider device, and/or any third-party service provider device.

Referring to FIG. 6A, illustrated is an embodiment of a user 602 viewing content using one or more user devices 300. In an example, the one or more user devices 300 includes a first user device 300A that may be mounted on the head of the user 602. The first user device 300A may include a screen for displaying content for the user, and may be used to collect various body information associated with the user 602, which will be described in detail below with reference to FIG. 6B. In another example, the one or more user devices 300 may include a second user device 300B that may be worn on a wrist of the user 602 or any other suitable places (e.g., hands, arms). The second user device 300B may be used to collect various body information associated with the user 602, which will be described in detail below with reference to FIG. 6C.

Referring to FIG. 6B, illustrated is an embodiment of a user device 300A of FIG. 6A that may be positioned on the head of the user 602 (e.g., an Oculus Rift® available from Oculus VR, LLC of Menlo Park, Calif.; a Samsung Gear VR® available from Samsung Electronics Co., Let of Suwon, South Korea; an HTC Vive® available from HTC Corp. of New Taipei City, Taiwan, Google Glass® available from Google Inc. of Mountain View, Calif.; etc.). The user device 300A includes a display 604 that may be used to display various content to the user, a camera 606 for capturing images of the user 602's face, and an infrared sensor 608 for capturing thermal images of the tear film 612 of the eye 610. In an example, the user device analyzes the face images to determine facial information including for example, eye blinking rate and eye redness information, using a digital image process engine. In another example, the user device analyzes the eye thermal images to determine facial information including eye dryness information by analyzing temperature change and temperature distribution on the tear film 612. The user device 300B may also include a Global Positioning System (GPS) device, a microphone, a wireless communications device, and/or any other subsystems that may be utilized to display content and capture the body information described herein.

Referring to FIG. 6C, illustrated is a user device 300B of FIG. 6A that may be worn on the user's wrist (e.g., a Fitbit Charge HR Wireless Activity Wristband® available from Fitbit Inc. of San Francisco, Calif.; an Apple Watch® available from Apple Inc. of Cupertino, Calif., etc.). The user device 300B includes a camera 640 that may be used to capture the user 602's facial information and/or gesture information, a perspiration sensor 642 that may be used to capture perspiration data of the user 602, a heart rate sensor 644 that may be used to capture a heart rate of the user 602, a motion sensor 646 that may be used to capture the user 602's gesture information, and a display 648 that may be used to display various content to the user. The user device 300B may also include a Global Positioning System (GPS) device, a microphone, a wireless communications device, and/or any other subsystems that may be utilized to capture the body information described herein.

Referring to FIG. 6D, illustrated is a user 602 viewing content using one or more user devices 300. In an example, the one or more user devices 300 include a laptop computing device 654 including a camera 650 that may be used to capture the user 602's facial information and/or gesture information. In another example, the one or more user device 300 include a camera 652 installed at a remote position relative to the laptop computing device 654 (e.g., on the ceiling of a room) and that is suitable to capture facial and gesture information of the user 602.

While the analysis of various images, gesture data, and body measurement data to recognize that the body information is associated with particular current health conditions of the user has been discussed as being performed in the user device 300, in some embodiments, the image file, the gesture data, and/or body measurement data may be sent to the system provider device (e.g., through a network) and then analyzed (e.g., by an imaging processing engine) in the system provider device to determine the corresponding current health conditions while remaining within the scope of the present disclosure.

Referring to FIGS. 1, 6A, 6B, 6C, and 6D, the method 100 may proceed to block 110 where user device usage information and user body information are sent from the user device to the system provider device. In some embodiments, the user device usage information includes a length of a session that the user has been continuously using a user device.

Referring to FIG. 6B, in some examples, the user body information includes facial information of the user 602, for example, eye dryness information captured by the infrared sensor 608 of the user device 300A, eye redness information captured by the camera 606 of the user device 300A, and eye blinking/squinting rate captured by the camera 606 of the user device 300A.

Referring to FIG. 6C, in some examples, the body information may include gesture information corresponding to a gesture of the user 602 that is captured by the user device 300B. In some examples, the user 602 wears the user device 300B on the right wrist. In an example, the body information includes gesture information that is captured by a motion sensor 646 of the user device 300B and that is indicative of the user 602 raising their right hand. In another example, the body information includes gesture information that is captured by the camera 640 of the user device 300B and that is indicative of the user 602 raising their left hand. In some examples, the body information may include body measurement data of the user 602 such as perspiration data, heart rate data, temperature data, and/or any other body measurement data known in the art. In an example, the perspiration data of the user 602 is captured using the perspiration sensor 642 of the user device 300B. In another example, the heart rate data of the user 602 is captured using a heart rate sensor 644 of the user device 300B. In yet another example, the temperature data of the user 602 is captured using a temperature sensor of the user device 300B.

Referring to FIG. 6D, in some examples, the user body information includes facial information and/or gesture information of the user 602 captured by one or more cameras 650 and 652 of the one or more user devices 300.

Referring to FIGS. 1, 7A, and 7B, the method 100 may proceed to block 114 where the system provider device causes the user device to perform a user device management action. Various user device management actions may be performed based on the user device usage information and/or user body information according to the user device management configurations.

Referring to the example of FIG. 7A, an embodiment of a user device management action notification provided to the user device 300 is illustrated. As illustrated in the example of FIG. 7A, the user device 300 includes a display 302 displaying a user device management action notification screen 702. In the particular example of FIG. 7A, based on the user's medical history information, the system provider device 200 may determine that the user has a health condition indicating that the user received LASIK eye surgery. The system provider device 200 may then determine (e.g., by using a user device management configuration database) that user device management configuration 318 is associated with the user based on the health condition. In the particular example of FIG. 7A, the user device is a head-mounted device. As such, the head-mounted device management configuration 310 of the user device management configuration 318 applies, which provides a recommendation that the user may take a ten-minute break every thirty minutes when using the user device 300. The system provider device 200 sends a user device management action notification to the user device 300. As illustrated in FIG. 7A, the user device management action notification screen 702 includes a break reminder section 704 that notifies the user that the user has been using the user device 300 continuously for a prolonged period 706 (e.g., "THIRTY MINUTES"). The break reminder section 704 also includes a recommendation of a break of a particular break time 708 (e.g., "TEN-MINUTE") according to the head-mounted device management configuration 310. The user may select the button 710 (e.g., "TAKE A BREAK") to stop viewing the display of the user device 300. In an example, after the user selects the button 710, the user device 300 is turned off or switched to a sleep mode for the particular break time 708. Alternatively, in some examples, the user chooses to continue using the device but take a break later, and selects the button 712 (e.g., "REMIND AGAIN IN FIVE MINUTES"). In an example, after the user selects the button 712, the user device 300 may continue to display content to the user, and after five minutes, display a break reminder to the user again.

In some embodiments, as illustrated in FIG. 7B, the user may not be provided the ability to change or delay the user device management action. Referring to the example of FIG. 7B, an embodiment of a user device management action notification is provided to the user device 300. As illustrated in the example of FIG. 7B, the user device 300 includes a display 302 displaying a user device management action notification screen 702. In the particular example of FIG. 7B, based on the user's medical history information, the system provider device 200 may determine that the user has a health condition indicating that the user received LASIK eye surgery previously. The system provider device 200 may then determine (e.g., by using a user device management configuration database) that user device management configuration 410 is associated with the user based on the health condition. The user device management configuration 410 provides that the user device will be switched to sleep mode for ten minutes after the system provider device receives body information 404 indicating that the user has a high blinking/squinting rate (e.g., greater than about 10 times/minute).

In the particular example of FIG. 7B, the system provider device 200 receives body information 404 from the user device 300 indicating that the user has a blinking/squinting rate of about 15 times/minute. The system provider device 200 may then determine a user device management action based on the body information according to the user device management configuration 410, and send a user device management action notification to the user device 300. As illustrated in FIG. 7B, the user device management action notification screen 702 includes a notification section 724 (e.g., "SWITCH TO SLEEP MODE NOTIFICATION"), which includes health information 726 (e.g., "YOUR EYES ARE TIRED") of the user determined using the body information, and a user device management action 728 (e.g., "SWITCHED TO SLEEP MODE") notifying the user that the user device 300 will be switched to the sleep mode for a time period 730 (e.g., "10 MINUTES"). In such example, the user may not be provided the ability to change or delay the user device management action, and the user device 300 will be switched to the sleep mode for about ten minutes in thirty seconds.

Referring to FIGS. 1, 8A, 8B, 9A, and 9B, the method 100 proceeds to block 116, where a content management action is performed based on the user body information according to content management configurations. In some embodiments, the system provider device determines that an operator (e.g., a teacher provided for live course content) associated with a content service provider is available for managing content. In such embodiments, the system provider device may determine user engagement information based on the user body information, and provide the user engagement information to an operator device (e.g., a teacher device). The operator may manage the content for the user based on the user engagement information. In some embodiments, the system provider device and/or the content provider device may automatically make adjustments to the content displayed to the user based on the user body information.

Figure 8A:
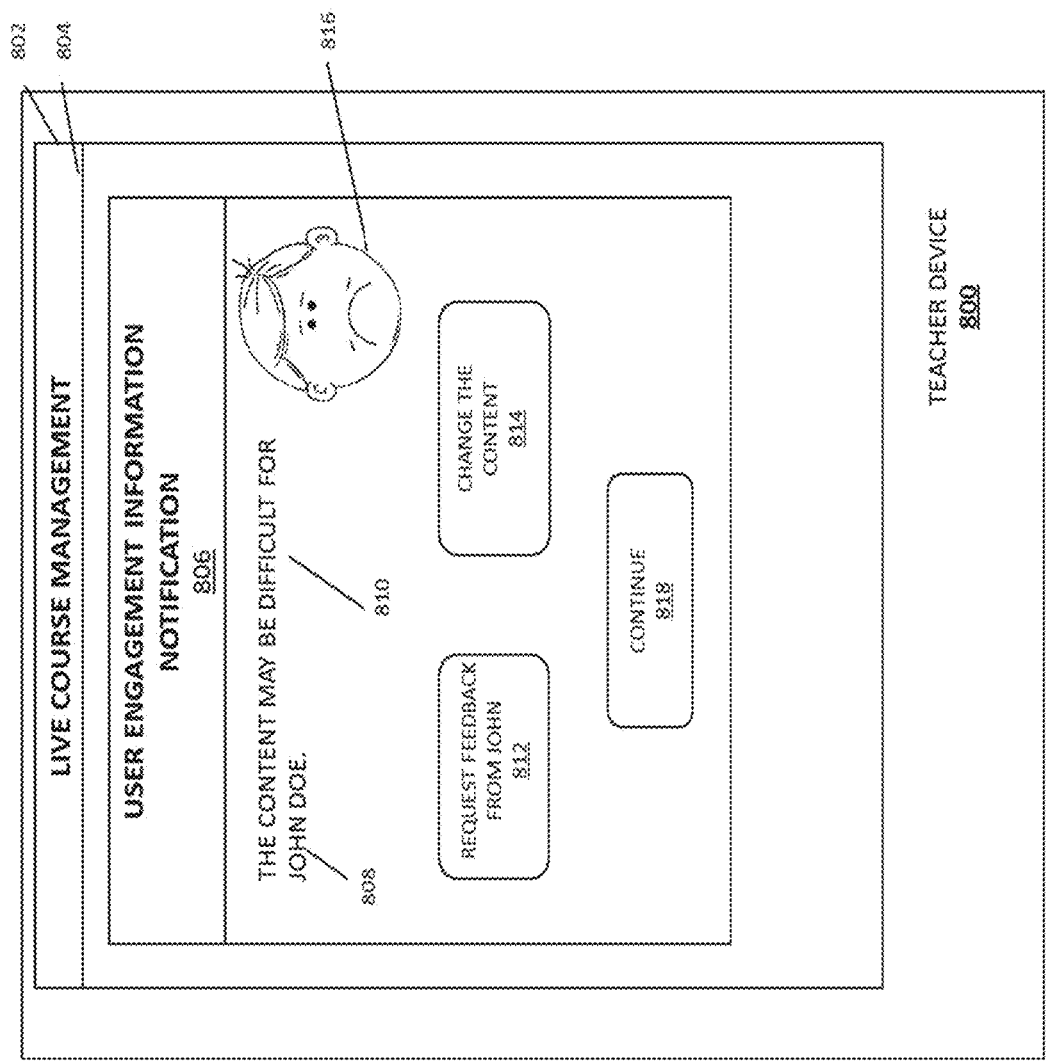
FIG. 8A is a screen shot illustrating an embodiment of a teacher device displaying a user engagement information notification screen.
Figure 8B:
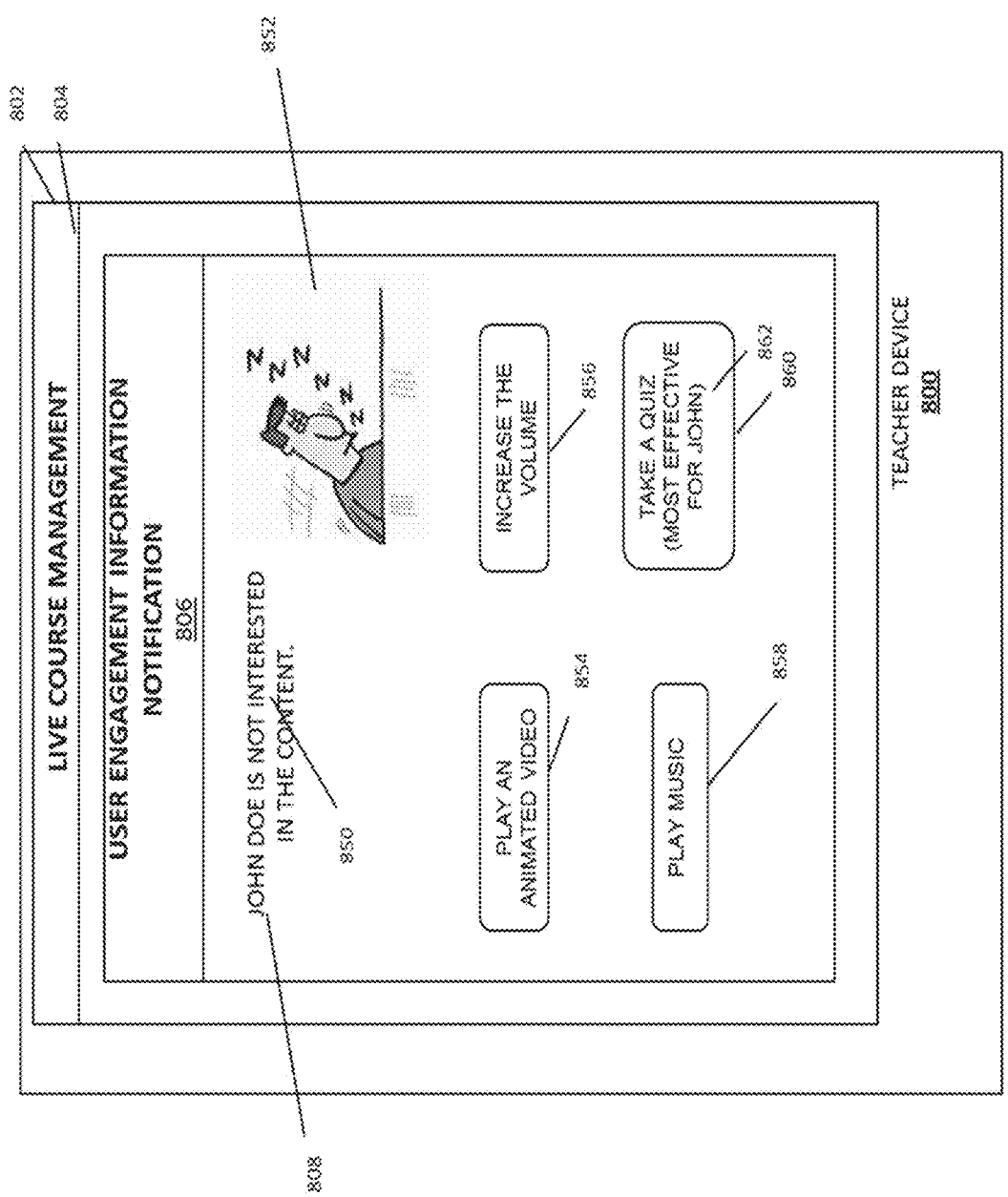
FIG. 8B is a screen shot illustrating an embodiment of a teacher device displaying a user engagement information notification screen.

Referring to FIGS. 8A and 8B, illustrated are embodiments of an operator device (e.g., a teacher device) associated with an operator (e.g., a teacher) for managing content (e.g., live course content) provided to a user based on user engagement information provided by the system provider device. In some embodiments, the user engagement information may include content difficulty level information that indicates whether the user finds that the content is too difficult, too easy, or at the right difficulty level. In some embodiments, the user engagement information may include user interest level information that indicates whether the user finds that the content is interesting or has been distracted.

Referring to FIG. 8A, illustrated is an embodiment of a teacher device 800 including a display 802 displaying a live course management screen 804 that includes a user engagement information notification section 806. In an example, the system provider device receives body information 404 (e.g., frowning facial information) from the user device, indicating that the user is frowning when viewing the content. The system provider device may determine user engagement information (e.g., "CONTENT IS DIFFI- CULT") based on the body information 404 according to the content management configuration 506 as discussed above with reference to FIG. 5. The system provider device further may determine that the content is associated with a live course, perform a live course management action 520 (e.g., "PROVIDE NOTIFICATION INDICATING USER ENGAGEMENT") of the content management configuration 506, and send a user engagement information notification to a teacher device. As illustrated in FIG. 8A, the user engagement information notification section 806 includes user engagement information 810 (e.g., "THE CONTENT MAY BE DIFFICULT") associated with a user 808 (e.g., "JOHN DOE"). The user engagement information notification section 806 may also include an image 816 of the user so that the teacher may use the image 816 to further determine the content's difficulty level for the user. In some embodiments, the teacher may perform various actions based on the user engagement information (e.g., user engagement information 810 received from the system provider device, and/or user engagement information that the teacher extracted from the image 816). In an example, the teacher may select the button 812 (e.g., "REQUEST FEEDBACK FROM JOHN") to request feedback from the user 808 (e.g., confirming the difficulty level of the content, and/or collecting questions from the user). In another example, the teacher may select the button 814 (e.g., "CHANGE THE CONTENT") to adapt the content based on the user's engagement information (e.g., by providing more detailed explanation of a particular topic where the user finds the content difficult). Yet in another example, the teacher may select the button 818 (e.g., "CONTINUE") without making any changes to the content (e.g., after the teacher determines there is no need to make changes to the content based on the difficult level shown by the user's image 816).

Referring to FIG. 8B, in some embodiments, the user engagement information includes user interest level information. Illustrated in FIG. 8B is an embodiment of a teacher device 800 that includes a display 802 displaying a live course management screen 804 that includes a user engagement information notification section 806. In the example of FIG. 8B, the system provider device receives body information 404 (e.g., a nodding off gesture information) from the user device that indicates that the user is nodding off. The system provider device may determine user engagement information (e.g., "NOT INTERESTED IN CONTENT") based on the body information 404 according to the content management configuration 508 as discussed above with reference to FIG. 5. In that particular example, the user engagement information includes user interest level information indicating that the user shows a low interest in the content (or a particular section of the content). The system provider device further may determine that the content is associated with live course content, perform a live course management action 520 (e.g., "PROVIDE NOTIFICATION INDICATING USER ENGAGEMENT") of the content management configuration 508, and send a user engagement information notification to a teacher device. As illustrated in FIG. 8B, the user engagement information notification section 806 includes user engagement information 850 (e.g., "NOT INTERESTED IN THE CONTENT") associated with a user 808 (e.g., "JOHN DOE"). The user engagement information notification section 806 may also include an image 852 of the user (e.g., showing the user's gesture), so that the teacher may use the image 852 to further determine the user's interest level in the content. In some embodiments, the teacher may perform various actions based on the user engagement information (e.g., user engagement information 850 received from the system provider device, and/or user engagement information that the teacher extracted from the image 852). In an example, the teacher may select the button 854 (e.g., "PLAY AN ANIMATED VIDEO") to play an animated video. In another example, the teacher may select the button 856 (e.g., "INCREASE THE VOLUME") to increase the volume of the sound played on the user device. In yet another example, the teacher may select the button 858 (e.g., "PLAY MUSIC") to play music on the user device. In yet another example, the teacher may select the button 860 (e.g., "TAKE A QUIZ") to start a quiz on the user device. In the example of FIG. 8B, the button 860 includes effectiveness information 862 (e.g., "MOST EFFECTIVE FOR JOHN") associated with the button 860. The effective information 862 may be determined based on past responses of the user for various changes to the content. In the particular example, the effectiveness information 862 provides that taking a quiz is the most effective way to regain the user's interest.

In some embodiments, after the teacher selects a button (e.g., from buttons 854, 856, 858, and 860) and makes a change to the content, the system provider device receives body information of the user in response to the change of the content, and updates the effectiveness information associated with those buttons based on that body information.

Figure 9A:
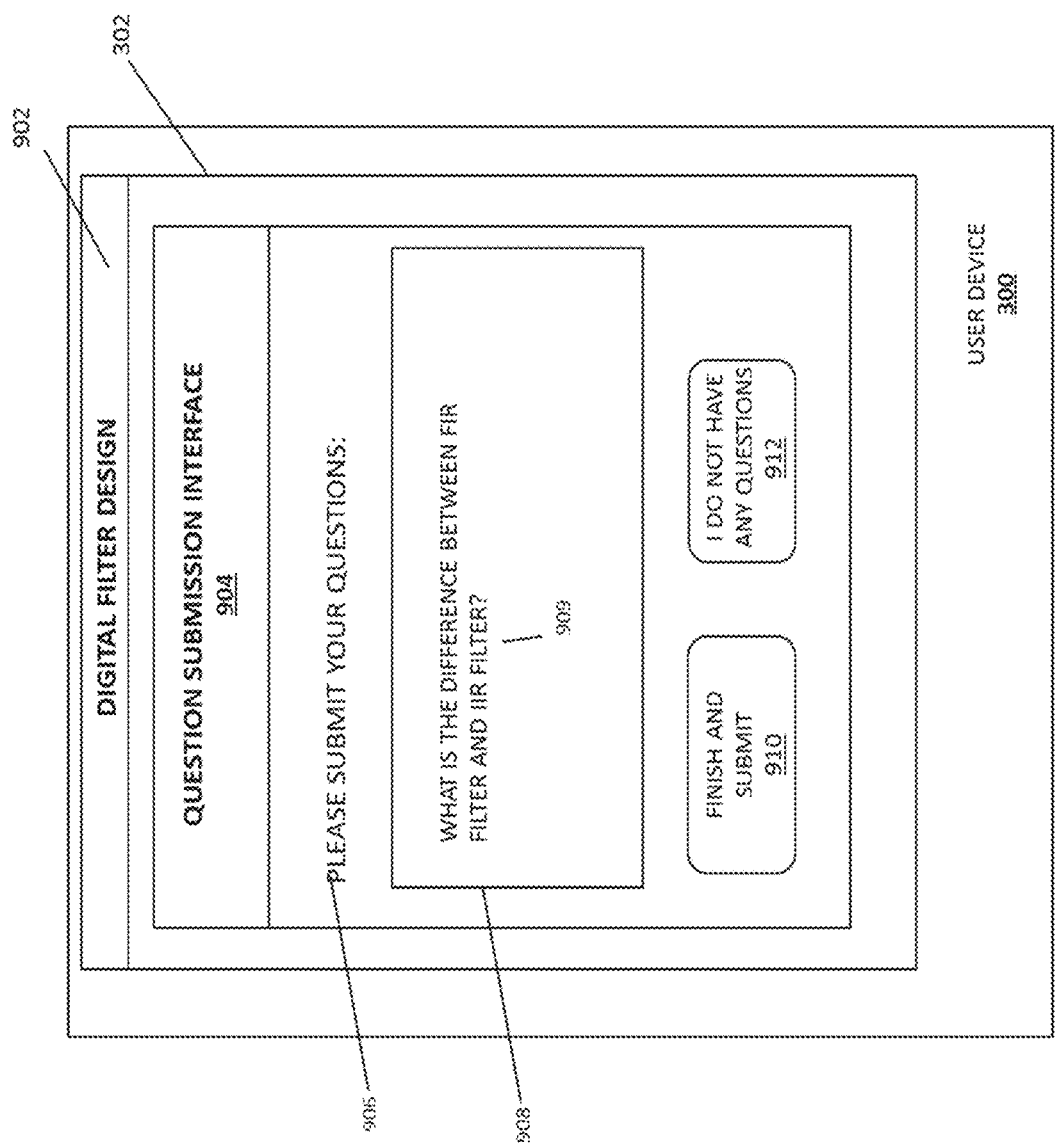
FIG. 9A is a screen shot illustrating an embodiment of a user device displaying an online course screen.

Referring to FIGS. 9A and 9B, in some embodiments, the system provider device and/or the content provider device may automatically make changes to the content based on the body information, the associated user engagement information, and the content management configurations. Illustrated in FIG. 9A is an embodiment of a user device 300 including a display 302 displaying an online course screen 902 associated with an online course (e.g., "DIGITAL FILTER DESIGN") that the user is taking. The system provider device receives body information 404 (e.g., a raising a hand gesture information) from the user device, and determines user engagement information (e.g., "REQUEST FOR ASKING QUESTIONS") based on the body information 404 according to the content management configuration 510 as discussed above with reference to FIG. 5. The system provider device further may determine that the content is associated with recorded course content, and perform a recorded course management action 522 (e.g., "PAUSE THE COURSE; PROVIDE A QUESTION SUBMISSION INTERFACE TO THE USER") of the content management configuration 510. According to the recorded course management action 522 of the content management configuration 510, the system provider device may pause the recorded course displayed on the user device 300, and cause the user device 300 to display a question submission interface 904 in the online course screen 902. The question submission interface 904 includes a message 906 (e.g., "PLEASE SUBMIT YOUR QUESTIONS"), and an input area 908 where the user may type questions. In the particular example, the user has typed a question 909 (e.g., "WHAT IS THE DIFFERENCE BETWEEN FIR FILTER AND IIR FILTER?"). In an example, after the user has finished with the questions, the user chooses the button 910 (e.g., "FINISH AND SUBMIT") to submit the questions to the system provider device and/or the content provider device. In another example, the user chooses the button 912 (e.g., "I DO NOT HAVE ANY QUESTIONS") without providing any questions. In such examples, the recorded course is resumed without any changes.

Referring to FIG. 9B, in some embodiments, after the system provider device and/or the content provider device receives the question 909 from the user device 300, the system provider device and/or the content provider device automatically update the online course material with content associated with the question 909, and sends a content change notification to the user device 300 that causes the updated online course content to be displayed on the user device 300. Illustrated in FIG. 9B is an embodiment of a user device 300 including a display 302 displaying an online course screen 902 associated with the online course (e.g., "DIGITAL FILTER DESIGN"). The online course screen 902 includes an updated online course content section 950 (e.g., "DIFFERENCE BETWEEN FIR FILTERS AND IIR FILTERS"), which displays content 952 addressing the user's question 909.

It is noted that while online course content providers are used as an example of content providers, it is not intended to be limiting. A variety of other content providers (e.g., online news and blogs providers, online game providers, merchant website providers, social media providers) may be used in the method 100 without departing from the scope of the present disclosure. For example, a merchant website provider may receive user engagement information associated with particular content (e.g., online instruction manual content) indicating that the users find that the particular content are difficult to understand. In response, the merchant website provider may update the particular content to boost user engagement, which may lead to more sales of products.

Thus, systems and methods for providing device and content management have been described that operate to provide users, system providers, and various content providers a device and content management system that may adapt device and content management according to needs of different users. The device and content management may be configured based on the user's health conditions, including pre-existing health conditions, current health conditions, and/or a combination thereof. For example, the system provider device may determine pre-existing health conditions of the user using medical history information associated with user. For further example, the system provider device may determine current health conditions of the user based on body information (e.g., facial information, gesture information, body measurement data, and/or a combination thereof) captured by the user devices. The system provider device may control the user device usage (e.g. the length of a continuous usage session, the length of a break between two continuous usage sessions, brightness of the display, volume of the sound) based on those health conditions. This allows the system provider device to provide personalized health protection for the user based on the user's health conditions.

In some embodiments, the device and content management is configured based on user engagement information in content displayed on the user device. For example, the system provider device may determine user engagement information (e.g., content difficulty level, user interest level, user request for asking questions) based on body information (e.g., facial information, gesture information, body measurement data) captured by a user device. The system provider device may control the content displayed on the user device (e.g., directly or through a content provider device) based on the user engagement information. This allows the system provider device to provide personalized content to the user, and improve user engagement in the content.

Figure 10:
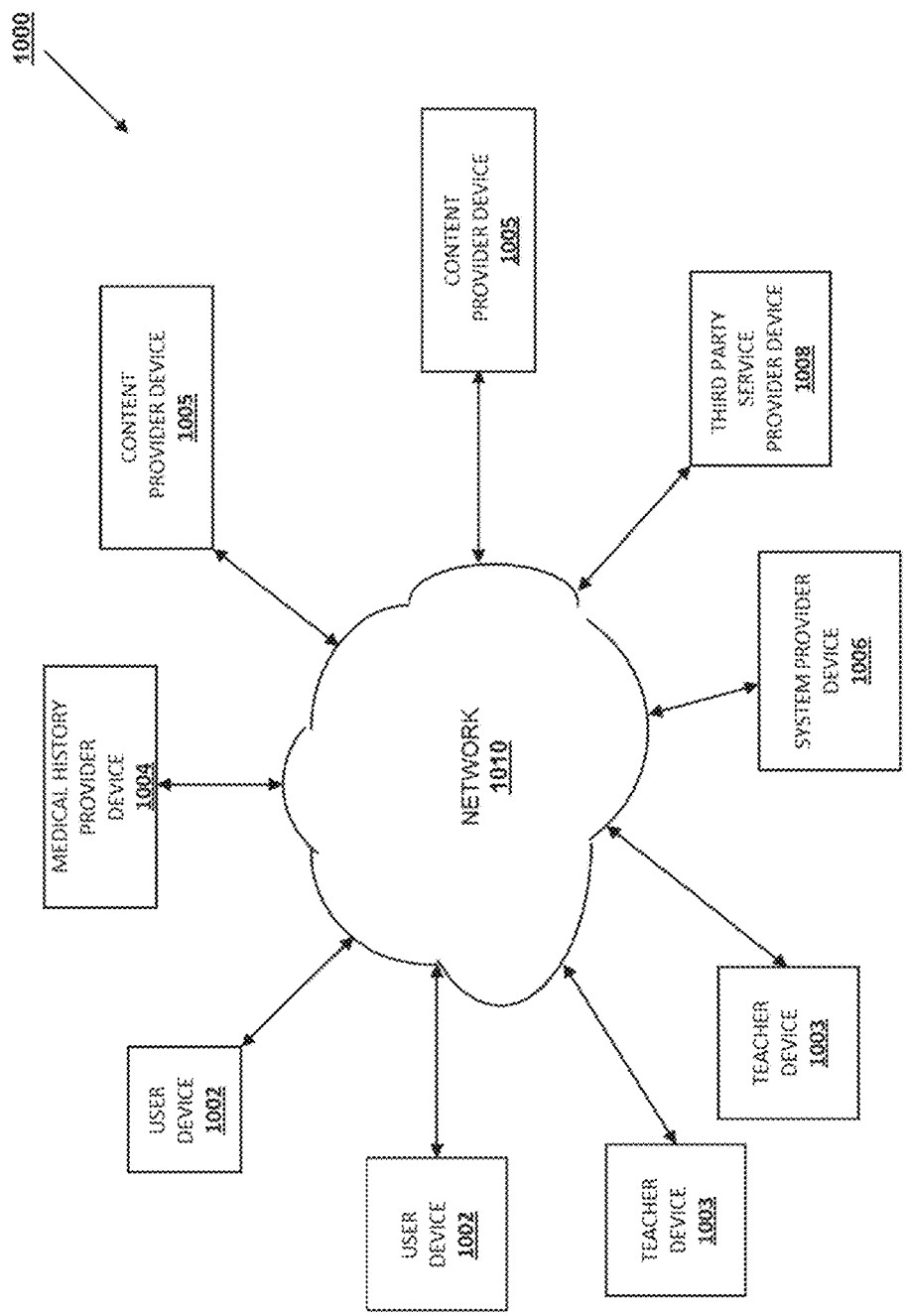
FIG. 10 is a schematic view illustrating an embodiment of a networked system.

Referring now to FIG. 10, an embodiment of a network-based system 1000 for implementing one or more processes described herein is illustrated. As shown, network-based system 1000 may comprise or implement a plurality of servers and/or software components that operate to perform various methodologies in accordance with the described embodiments. Exemplary servers may include, for example, stand-alone and enterprise-class servers operating a server OS such as a MICROSOFT® OS, a UNIX® OS, a LINUX® OS, or other suitable server-based OS. It can be appreciated that the servers illustrated in FIG. 10 may be deployed in other ways and that the operations performed and/or the services provided by such servers may be combined or separated for a given implementation and may be performed by a greater number or fewer number of servers. One or more servers may be operated and/or maintained by the same or different entities.

The embodiment of the networked system 1000 illustrated in FIG. 10 includes one or more user devices 1002, one or more teacher devices 1003, one or more medical history provider devices 1004, one or more content provider devices 1005, one or more system provider devices 1006, and one or more third party service provider devices 1008 in communication over a network 1010. Any of the user devices 1002 may be the user devices 300, 300A, and 300B discussed above and used by the user discussed above. Any of the teacher devices 1003 may be the teacher device 800 associated with the teacher discussed above. Any of the medical history provider devices 1004 may be the medical history provider device associated with the medical history provider discussed above. Any of the content provider devices 1005 may be the content provider device 500 discussed above and associated with the content provider discussed above. The system provider device 1006 may be the system provider device 200 discussed above and may be operated by a system provider such as, for example, PayPal Inc. of San Jose, Calif. The third party service provider device 1008 may be the service provider device discussed above and may be operated by various service providers including payment service providers, rewards providers, discount providers, marketplace providers, and/or any other service providers.

The user devices 1002, teacher devices 1003, medical history provider devices 1004, content provider devices 1005, system provider devices 1006, and third party service provider devices 1008 may each include one or more processors, memories, and other appropriate components for executing instructions such as program code and/or data stored on one or more computer readable mediums to implement the various applications, data, and steps described herein. For example, such instructions may be stored in one or more computer readable mediums such as memories or data storage devices internal and/or external to various components of the system 1000, and/or accessible over the network 1010.

The network 1010 may be implemented as a single network or a combination of multiple networks. For example, in various embodiments, the network 1010 may include the Internet and/or one or more intranets, landline networks, wireless networks, and/or other appropriate types of networks.

The user device 1002 may be implemented using any appropriate combination of hardware and/or software configured for wired and/or wireless communication over network 1010. For example, in one embodiment, the user device 1002 may be implemented as a personal computer of a user in communication with the Internet. In some embodiments, the user device 1002 may be a wearable device. In some embodiments, the user device 1002 may be a smart phone, personal digital assistant (PDA), laptop computer, and/or other types of computing devices.

The user device 1002 may include one or more browser applications which may be used, for example, to provide a convenient interface to permit the customer to browse information available over the network 1010. For example, in one embodiment, the browser application may be implemented as a web browser configured to view information available over the Internet.

The user device 1002 may also include one or more toolbar applications which may be used, for example, to provide user-side processing for performing desired tasks in response to operations selected by the customer. In one embodiment, the toolbar application may display a user interface in connection with the browser application.

The user device 1002 may further include other applications as may be desired in particular embodiments to provide desired features to the user device 1002. In particular, the other applications may include an online course application provided by an online course provider through the content provider device 1005. The other applications may also include security applications for implementing user-side security features, programmatic user applications for interfacing with appropriate application programming interfaces (APIs) over the network 1010, or other types of applications. Email and/or text applications may also be included, which allow the customer to send and receive emails and/or text messages through the network 1010. The user device 1002 includes one or more user and/or device identifiers which may be implemented, for example, as operating system registry entries, cookies associated with the browser application, identifiers associated with hardware of the user device 1002, or other appropriate identifiers, such as a phone number. In one embodiment, the user identifier may be used by the system provider device 1006, the medical history provider device 1004, and/or the content provider device 1005 to associate the user with a particular account as further described herein.

Figure 11:
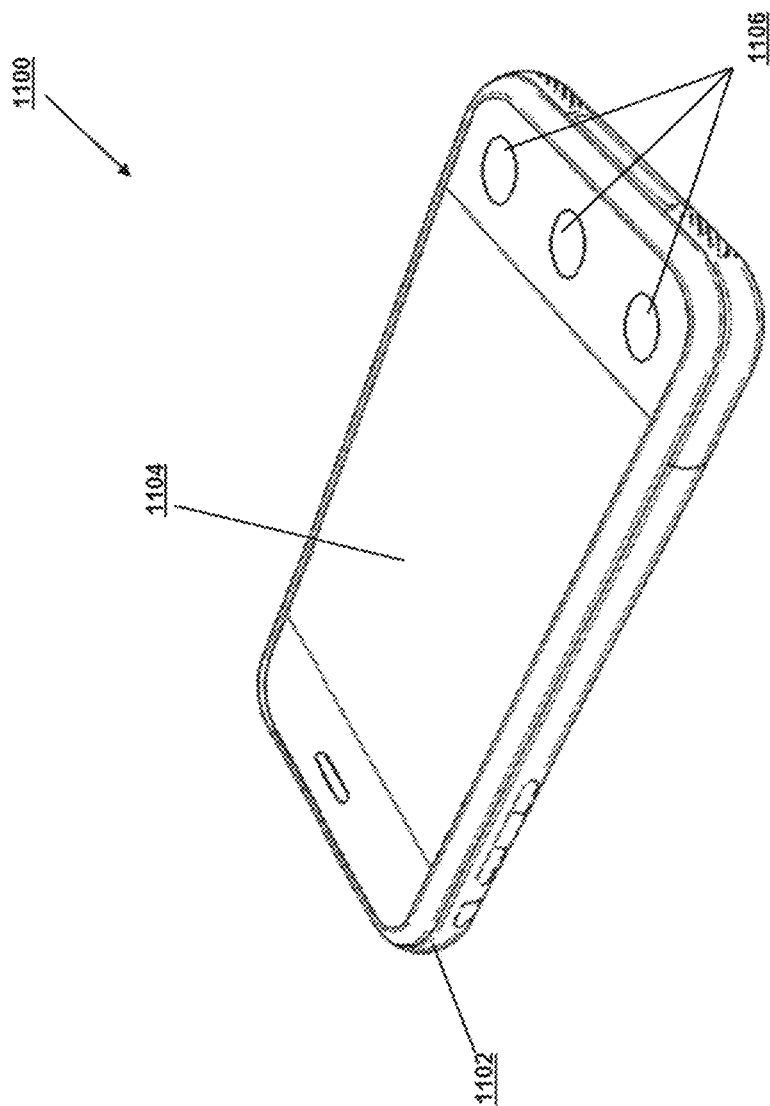
FIG. 11 is a perspective view illustrating an embodiment of a user device.

Referring now to FIG. 11, an embodiment of a user device 1100 is illustrated. The user device 1100 may be the user devices 300, 300A, and 300B. The user device 1100 includes a chassis 1102 having a display 1104 and an input device including the display 1104 and a plurality of input buttons 1106. One of skill in the art will recognize that the user device 1100 is a portable or mobile phone including a touch screen input device and a plurality of input buttons that allow the functionality discussed above with reference to the method 100. However, a variety of other portable/mobile customer devices may be used in the method 100 without departing from the scope of the present disclosure.

Figure 12:
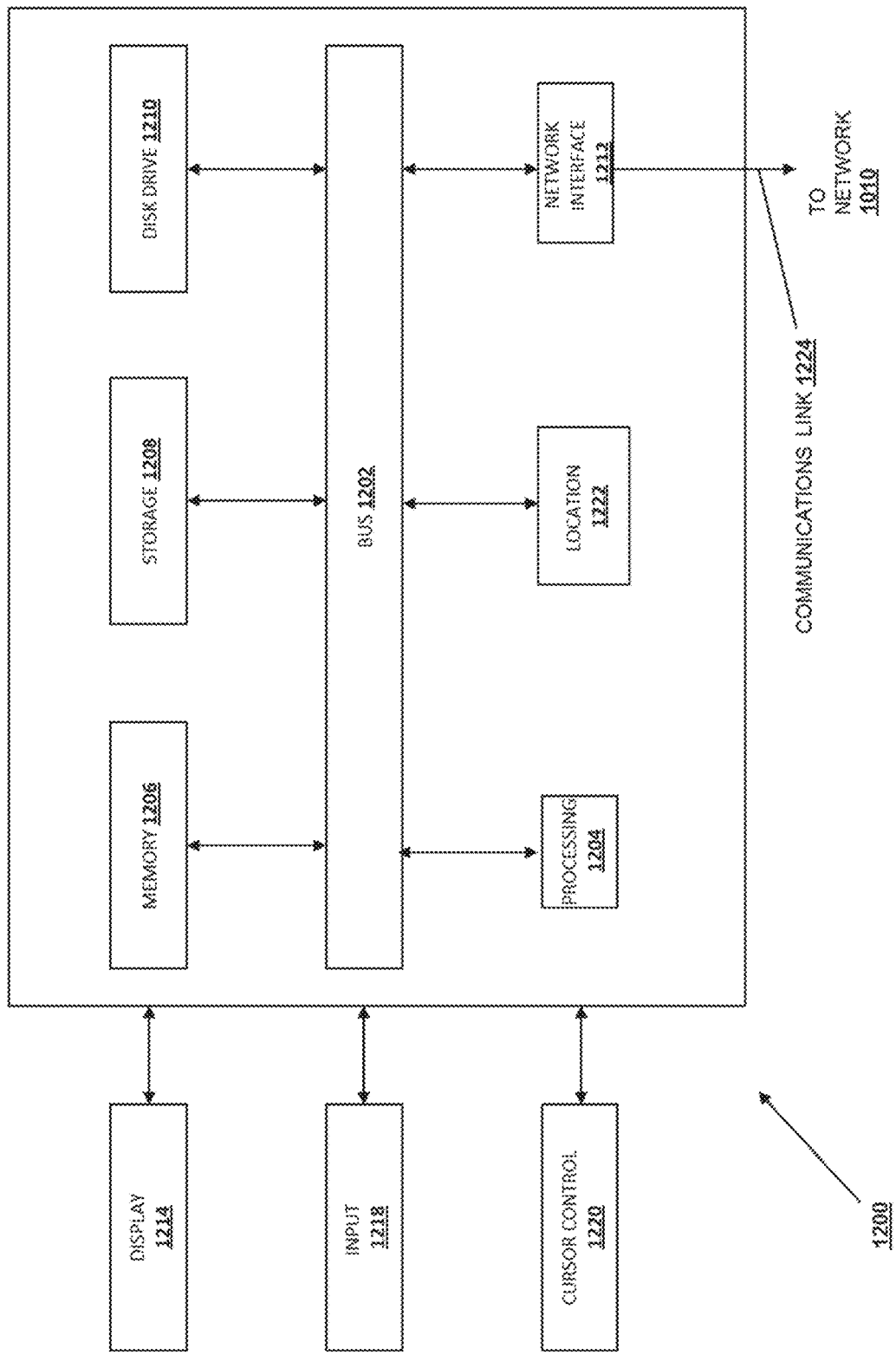
FIG. 12 is a schematic view illustrating an embodiment of a computer system.

Referring now to FIG. 12, an embodiment of a computer system 1200 suitable for implementing, for example, the system provider device 200, user devices 300, 300A, and 300B, content provider device 500, teacher device 800, medical history provider device 1004, content provider device 1005, third party service provider device 1008, is illustrated. It should be appreciated that other devices utilized by users, teachers, content providers, medical history providers, third party service providers, and/or system providers in the system discussed above may be implemented as the computer system 1200 in a manner as follows.

In accordance with various embodiments of the present disclosure, computer system 1200, such as a computer and/or a network server, includes a bus 1202 or other communication mechanism for communicating information, which interconnects subsystems and components, such as a processing component 1204 (e.g., processor, micro-controller, digital signal processor (DSP), etc.), a system memory component 1206 (e.g., RAM), a static storage component 1208 (e.g., ROM), a disk drive component 1210 (e.g., magnetic or optical), a network interface component 1212 (e.g., modem or Ethernet card), a display component 1214 (e.g., CRT or LCD), an input component 1218 (e.g., keyboard, keypad, or virtual keyboard), a cursor control component 1220 (e.g., mouse, pointer, or trackball), and a location sensor component 1222 (e.g., a Global Positioning System (GPS) device as illustrated, a cell tower triangulation device, and/or a variety of other location determination devices known in the art). In one implementation, the disk drive component 1210 may comprise a database having one or more disk drive components.

In accordance with embodiments of the present disclosure, the computer system 1200 performs specific operations by the processor 1204 executing one or more sequences of instructions contained in the memory component 1206, such as described herein with respect to the system provider device(s) 200, user devices 300, 300A, and 300B, content provider device 500, teacher devices 800, medical history provider device 1004, content provider device 1005, and/or third party service provider device 1008. Such instructions may be read into the system memory component 1206 from another computer readable medium, such as the static storage component 1208 or the disk drive component 1210. In other embodiments, hard-wired circuitry may be used in place of or in combination with software instructions to implement the present disclosure.

Logic may be encoded in a computer readable medium, which may refer to any medium that participates in providing instructions to the processor 1204 for execution. Such a medium may take many forms, including but not limited to, non-volatile media, volatile media, and transmission media. In one embodiment, the computer readable medium is non-transitory. In various implementations, non-volatile media includes optical or magnetic disks, such as the disk drive component 1210, volatile media includes dynamic memory, such as the system memory component 1206, and transmission media includes coaxial cables, copper wire, and fiber optics, including wires that comprise the bus 1202. In one example, transmission media may take the form of acoustic or light waves, such as those generated during radio wave and infrared data communications.

Some common forms of computer readable media includes, for example, floppy disk, flexible disk, hard disk, magnetic tape, any other magnetic medium, CD-ROM, any other optical medium, punch cards, paper tape, any other physical medium with patterns of holes, RAM, PROM, EPROM, FLASH-EPROM, any other memory chip or cartridge, carrier wave, or any other medium from which a computer is adapted to read. In one embodiment, the computer readable media is non-transitory.

In various embodiments of the present disclosure, execution of instruction sequences to practice the present disclosure may be performed by the computer system 1200. In various other embodiments of the present disclosure, a plurality of the computer systems 1200 coupled by a communication link 1224 to the network 1010 (e.g., such as a LAN, WLAN, PTSN, and/or various other wired or wireless networks, including telecommunications, mobile, and cellular phone networks) may perform instruction sequences to practice the present disclosure in coordination with one another.

The computer system 1200 may transmit and receive messages, data, information and instructions, including one or more programs (i.e., application code) through the communication link 1224 and the network interface component 1212. The network interface component 1212 may include an antenna, either separate or integrated, to enable transmission and reception via the communication link 1224. Received program code may be executed by processor 1204 as received and/or stored in disk drive component 1210 or some other non-volatile storage component for execution.

Figure 13:
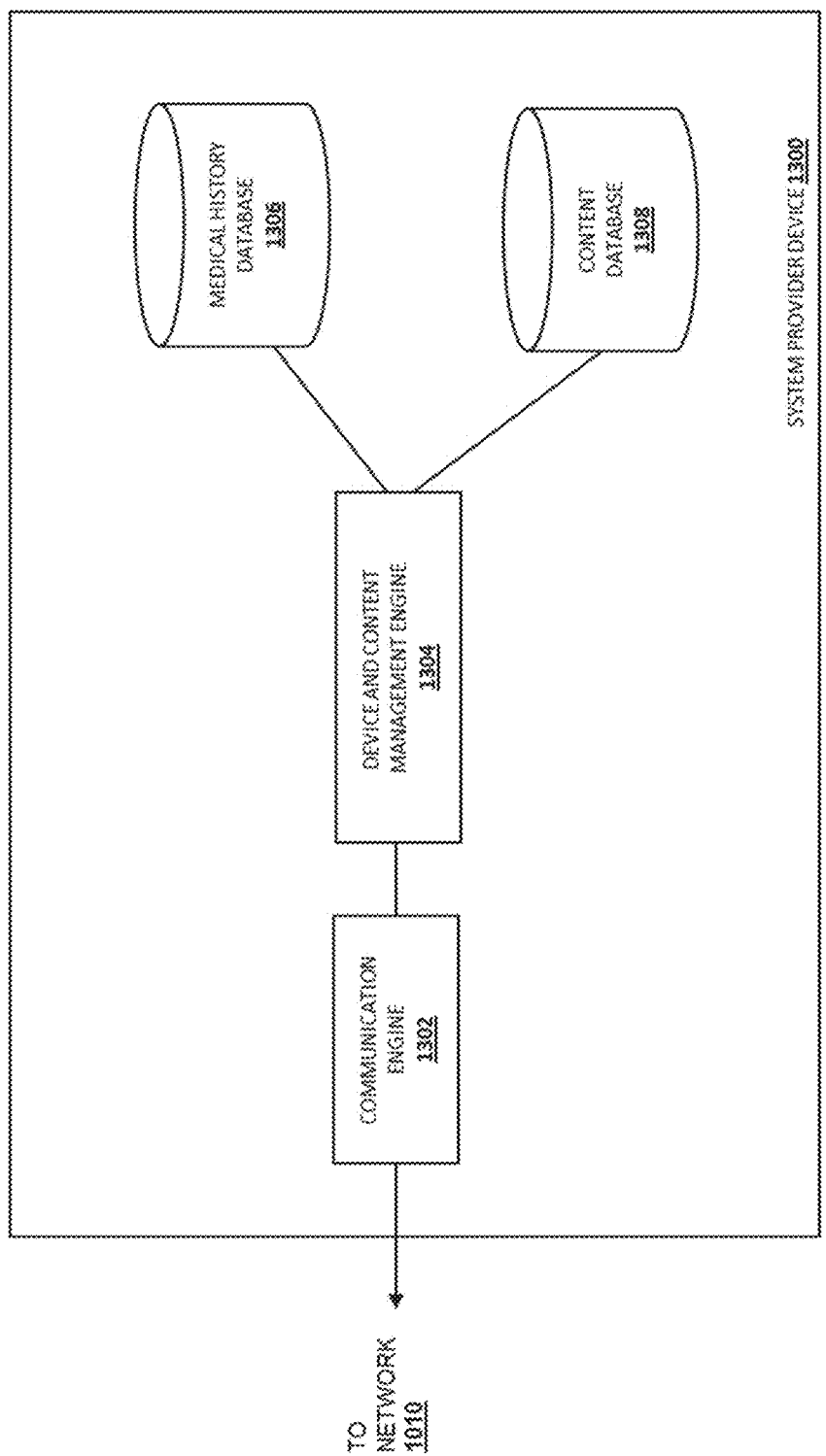
FIG. 13 is a schematic view illustrating an embodiment of a system provider device.

Referring now to FIG. 13, an embodiment of a system provider device 1300 is illustrated. In an embodiment, the system provider device 1300 may be the system provider devices 200 discussed above. The system provider device 1300 includes a communication engine 1302 that is coupled to the network 1010 and to a device and content management engine 1304 that is coupled to a medical history database 1306 and a content database 1308. The communication engine 1302 may be software or instructions stored on a computer-readable medium that allows the system provider device 1300 to send and receive information over the network 1010. The device and content management engine 1304 may be software or instructions stored on a computer-readable medium that is operable to receive body information from a user device associated with a user, determine a user device management configuration associated with the body information, retrieve a user device management action using the user device management configuration, and send to the user device, a notification associated with the user device management action that causes the user device to perform the user device management action, and provide any of the other functionality that is discussed above. While the databases 1306-1308 have been illustrated as separate from each other and located in the system provider device 1300, one of skill in the art will recognize that any or all of the databases 1306-1308 may be combined and/or may be connected to the device and content management engine 1304 through the network 1010 without departing from the scope of the present disclosure.

Where applicable, various embodiments provided by the present disclosure may be implemented using hardware, software, or combinations of hardware and software. Also, where applicable, the various hardware components and/or software components set forth herein may be combined into composite components comprising software, hardware, and/or both without departing from the scope of the present disclosure. Where applicable, the various hardware components and/or software components set forth herein may be separated into sub-components comprising software, hardware, or both without departing from the scope of the present disclosure. In addition, where applicable, it is contemplated that software components may be implemented as hardware components and vice-versa.

Software, in accordance with the present disclosure, such as program code and/or data, may be stored on one or more computer readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein.

The foregoing disclosure is not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, persons of ordinary skill in the art will recognize that changes may be made in form and detail without departing from the scope of the present disclosure. Thus, the present disclosure is limited only by the claims.

The foregoing disclosure is not intended to limit the present disclosure to the precise forms or particular fields of use disclosed. As such, it is contemplated that various alternate embodiments and/or modifications to the present disclosure, whether explicitly described or implied herein, are possible in light of the disclosure. Having thus described embodiments of the present disclosure, persons of ordinary skill in the art will recognize that changes may be made in form and detail without departing from the scope of the present disclosure. Thus, the present disclosure is limited only by the claims.

What is claimed is:

1. A system, comprising:
a non-transitory memory; and
one or more hardware processors coupled to the non-transitory memory and configured to read instructions from the non-transitory memory to cause the system to perform operations comprising:
determining a user is performing a first task using a user device;
receiving, by a system provider device through a network, medical history information associated with the user;
determining, by the system provider device, a user device management configuration based on the medical history information;
receiving, by the system provider device through the network from the user device, user device usage information associated with the user;
determining, by the system provider device, a user device management action based on the user device usage information and the user device management configuration, and
sending, through the network to the user device, a notification associated with the user device management action that causes the user device to perform the user device management action.

2. The system of claim 1, wherein the operations further comprise:
determining a pre-existing health condition associated with the user using the medical history information, wherein the user device management action is further based on the pre-existing health condition.

3. The system of claim 2, wherein the operations further comprise:
receiving, by the system provider device through the network from the user device, body information associated with the user; wherein the user device management action if further based on the body information.

4. The system of claim 3, wherein the pre-existing health condition includes a pre-existing heart health condition.

5. The system of claim 4, wherein the body information includes a heart rate greater than a heart rate threshold.

6. The system of claim 1, wherein the user device management action includes a user device break action.

7. A method, comprising:
determining a user is performing a first task using a user device;
receiving, by a system provider device through a network, medical history information associated with the user;
determining, by the system provider device, a user device management configuration based on the medical history information;

receiving, by the system provider device through the network from the user device, user device usage information associated with the user;

determining, by the system provider device, a user device management action comprising altering a visual content on the user device associated with the first task based on the user device usage information and the user device management configuration, and causing the user device management action to be performed on the user device.

8. The method of claim 7, further comprising:
determining a pre-existing health condition associated with the user based on the medical history information, wherein the user device management action is further based on the pre-existing health condition.

9. The method of claim 8, further comprising:
receiving, by the system provider device through the network from the user device, body information associated with the user, wherein the user device management action is further based on the body information.

10. The method of claim 9, wherein the body information includes facial information associated with eye stress.

11. The method of claim 10, wherein the facial information is selected from the group consisting of eye blinking rate information, eye redness information, and eye dryness information.

12. The method of claim 10, further comprising:
generating thermal images of tear films of the user using an infrared sensor of the user device; and
generating eye dryness information using the thermal images.

13. The method of claim 8, wherein the pre-existing health condition includes a pre-existing eye health condition.

14. The method of claim 7, wherein the user device management configuration is associated with a viewing distance between a display of the user device and an eye of the user.

15. The method of claim 7, wherein the user device management action is selected from the group consisting of switching off a display of the user device, changing brightness with one or more images of content on the display, changing sizes of texts and images of the content, and changing a speed of image transitions of the content.

16. A non-transitory machine-readable medium having stored thereon machine-readable instructions executable to cause a machine to perform operations comprising:
determining a user is performing a first task using a user device;
receiving, by a system provider device through a network from a medical history provider device associated with a medical history provider, medical history information associated with the user;
determining, by the system provider device, a user device management configuration based on the medical history information;
receiving, by the system provider device through the network from the user device, user device usage information associated with the user;
determining, by the system provider device, a user device management action based on the user device usage information, the first task, and the user device management configuration, and
causing the user device management action to be performed on the user device.

17. The non-transitory machine-readable medium of claim 16, wherein the operations further comprise:
determining a pre-existing health condition associated with the user using the medical history information, wherein the user device management action comprises a change to content being displayed on or audio played through the user device and is further based on the pre-existing health condition.

18. The non-transitory machine-readable medium of claim 16, wherein the operations further comprise:
receiving, by the system provider device through the network from the user device, body information associated with the user, wherein the user device management action is further based on the body information.

19. The non-transitory machine-readable medium of claim 16, wherein the user device management action is selected from the group consisting of switching off a display of the user device, changing brightness with one or more images of content on the display, changing sizes of texts and images of the content, and changing a speed of image transitions of the content.

20. The non-transitory machine-readable medium of claim 19, wherein the display is a head-mounted display configured to be worn on a head of the user.

* * * * *